US012640275B2

(12) United States Patent
Jacobson et al.

(10) Patent No.: US 12,640,275 B2
(45) Date of Patent: May 26, 2026

(54) INFUSION PUMP SYSTEM AND METHOD WITH MULTIPLE DRUG LIBRARY EDITOR SOURCE CAPABILITY

(71) Applicant: ICU Medical, Inc., San Clemente, CA (US)

(72) Inventors: James D. Jacobson, Lindenhurst, IL (US); Anatoly S. Belkin, Glenview, IL (US)

(73) Assignee: ICU Medical, Inc., San Clemente, CA (US)

( * ) Notice: Subject to any disclaimer, the term of this patent is extended or adjusted under 35 U.S.C. 154(b) by 327 days.

(21) Appl. No.: 18/181,348

(22) Filed: Mar. 9, 2023

(65) Prior Publication Data

US 2023/0298768 A1 Sep. 21, 2023

Related U.S. Application Data

(63) Continuation of application No. 15/164,251, filed on May 25, 2016, now Pat. No. 11,605,468.
(Continued)

(51) Int. Cl.
*A61M 5/172* (2006.01)
*G16H 20/17* (2018.01)
(Continued)

(52) U.S. Cl.
CPC ............ *G16H 70/40* (2018.01); *A61M 5/172* (2013.01); *G16H 20/17* (2018.01); *G16H 40/40* (2018.01); *A61M 2205/52* (2013.01)

(58) Field of Classification Search
CPC .. A61M 5/172; A61M 2205/52; G16H 70/40; G16H 20/17; G16H 40/40; G16H 40/63; G16H 40/67
See application file for complete search history.

(56) References Cited

U.S. PATENT DOCUMENTS

| | | | |
|---|---|---|---|
| 4,024,864 A | 5/1977 | Davies et al. | |
| 4,055,175 A | 10/1977 | Clemens et al. | |

(Continued)

FOREIGN PATENT DOCUMENTS

| | | |
|---|---|---|
| AU | 2004226440 | 10/2004 |
| AU | 2004305087 | 7/2005 |

(Continued)

OTHER PUBLICATIONS

Ahn et al., "Towards Scalable Authentication in Health Services", Eleventh IEEE International Workshops on Enabling Technologies: Infrastructure for Collaborative Enterprises, Jun. 2002, pp. 83-88.
(Continued)

*Primary Examiner* — Chelsea E Stinson
*Assistant Examiner* — Hing-Van N Trinh
(74) *Attorney, Agent, or Firm* — Knobbe, Martens, Olson & Bear, LLP

(57) ABSTRACT

An infusion pump system and method with multiple drug library editor source capability including: an infusion pump system having a first drug library editor operable to generate a first drug library; a second drug library editor operable to generate a second drug library; and an infusion pump operable to connect to either one of the first drug library editor and the second drug library editor, the infusion pump having an operational drug library being one of the first drug library received from the first drug library editor and the second drug library received from the second drug library editor. The first drug library editor is one of a dedicated drug library editor and an enterprise drug library editor, and the second drug library editor is the other of the one of the dedicated drug library editor and the enterprise drug library editor.

5 Claims, 6 Drawing Sheets

Related U.S. Application Data

(60) Provisional application No. 62/166,381, filed on May 26, 2015.

(51) Int. Cl.
  *G16H 40/40*    (2018.01)
  *G16H 70/40*    (2018.01)

(56)             References Cited

U.S. PATENT DOCUMENTS

| | | | |
|---|---|---|---|
| 4,151,845 | A | 5/1979 | Clemens |
| 4,213,454 | A | 7/1980 | Shim |
| 4,240,438 | A | 12/1980 | Updike et al. |
| 4,280,494 | A | 7/1981 | Cosgrove et al. |
| 4,308,866 | A | 1/1982 | Jeliffe |
| 4,370,983 | A | 2/1983 | Lichtenstein et al. |
| 4,373,527 | A | 2/1983 | Fischell |
| 4,392,849 | A | 7/1983 | Petre et al. |
| 4,395,259 | A | 7/1983 | Prestele et al. |
| 4,457,751 | A | 7/1984 | Rodler |
| 4,464,170 | A | 8/1984 | Clemens |
| 4,469,481 | A | 9/1984 | Kobayashi |
| 4,475,901 | A | 10/1984 | Kraegen et al. |
| 4,494,950 | A | 1/1985 | Fischell |
| 4,498,843 | A | 2/1985 | Schneider et al. |
| 4,515,584 | A | 5/1985 | Abe et al. |
| 4,526,568 | A | 7/1985 | Clemens et al. |
| 4,529,401 | A | 7/1985 | Leslie et al. |
| 4,543,955 | A | 10/1985 | Schroeppel |
| 4,551,133 | A | 11/1985 | Zegers de Beyl et al. |
| 4,553,958 | A | 11/1985 | LeCocq |
| 4,559,037 | A | 12/1985 | Franetzki et al. |
| 4,613,937 | A | 9/1986 | Batty |
| 4,624,661 | A | 11/1986 | Arimond |
| 4,633,878 | A | 1/1987 | Bombardieri |
| 4,634,426 | A | 1/1987 | kamen |
| 4,634,427 | A | 1/1987 | Hannula et al. |
| 4,674,652 | A | 6/1987 | Aten et al. |
| 4,676,776 | A | 6/1987 | Howson et al. |
| 4,679,562 | A | 7/1987 | Luksha |
| 4,685,903 | A | 8/1987 | Cable et al. |
| 4,695,954 | A | 9/1987 | Rose |
| 4,696,671 | A | 9/1987 | Epstein et al. |
| 4,714,462 | A | 12/1987 | DiDomenico |
| 4,722,734 | A | 2/1988 | Kolin |
| 4,730,849 | A | 3/1988 | Siegel |
| 4,731,051 | A | 3/1988 | Fischell |
| 4,741,732 | A | 5/1988 | Crankshaw et al. |
| 4,756,706 | A | 7/1988 | Kerns et al. |
| 4,776,842 | A | 10/1988 | Franetzki et al. |
| 4,785,969 | A | 11/1988 | McLaughlin |
| 4,803,625 | A | 2/1989 | Fu et al. |
| 4,835,372 | A | 5/1989 | Gombrich et al. |
| 4,838,275 | A | 6/1989 | Lee |
| 4,838,856 | A | 6/1989 | Mulreany et al. |
| 4,838,857 | A | 6/1989 | Strowe et al. |
| 4,854,324 | A | 8/1989 | Hirschman et al. |
| 4,857,716 | A | 8/1989 | Gombrich et al. |
| 4,858,154 | A | 8/1989 | Anderson et al. |
| 4,898,578 | A | 2/1990 | Rubalcaba, Jr. |
| 4,908,017 | A | 3/1990 | Howson et al. |
| 4,933,873 | A | 6/1990 | Kaufman et al. |
| 4,943,279 | A | 7/1990 | Samiotes et al. |
| 4,946,439 | A | 8/1990 | Eggers |
| 4,953,745 | A | 9/1990 | Rowlett |
| 4,978,335 | A | 12/1990 | Arthur, III |
| 5,000,739 | A | 3/1991 | Kulisz et al. |
| 5,010,473 | A | 4/1991 | Jacobs |
| 5,014,698 | A | 5/1991 | Cohen |
| 5,016,172 | A | 5/1991 | Dessertine |
| 5,026,084 | A | 6/1991 | Paisfield |
| 5,034,004 | A | 7/1991 | Crankshaw |
| 5,041,086 | A | 8/1991 | Koenig et al. |
| 5,058,161 | A | 10/1991 | Weiss |
| 5,078,683 | A | 1/1992 | Sancoff et al. |

| | | | |
|---|---|---|---|
| 5,084,828 | A | 1/1992 | Kaufman et al. |
| 5,088,981 | A | 2/1992 | Howson et al. |
| 5,097,505 | A | 3/1992 | Weiss |
| 5,100,380 | A | 3/1992 | Epstein et al. |
| 5,102,392 | A | 4/1992 | Sakai et al. |
| 5,104,374 | A | 4/1992 | Bishko et al. |
| 5,109,850 | A | 5/1992 | Blanco et al. |
| 5,131,816 | A | 7/1992 | Brown |
| 5,142,484 | A | 8/1992 | Kaufman et al. |
| 5,153,827 | A | 10/1992 | Coutre et al. |
| 5,157,640 | A | 10/1992 | Backner |
| 5,161,222 | A | 11/1992 | Montejo et al. |
| 5,177,993 | A | 1/1993 | Beckman et al. |
| 5,181,910 | A | 1/1993 | Scanlon |
| 5,190,522 | A | 3/1993 | Wocicki et al. |
| 5,199,439 | A | 4/1993 | Zimmerman et al. |
| 5,200,891 | A | 4/1993 | Kehr et al. |
| 5,216,597 | A | 6/1993 | Beckers |
| 5,221,268 | A | 6/1993 | Barton et al. |
| 5,230,061 | A | 7/1993 | Welch |
| 5,243,982 | A | 9/1993 | Möstl et al. |
| 5,244,463 | A | 9/1993 | Cordner, Jr. et al. |
| 5,249,260 | A | 9/1993 | Nigawara et al. |
| 5,254,096 | A | 10/1993 | Rondelet et al. |
| 5,256,156 | A | 10/1993 | Kern et al. |
| 5,256,157 | A | 10/1993 | Samiotes et al. |
| 5,261,702 | A | 11/1993 | Mayfield |
| 5,317,506 | A | 5/1994 | Coutre et al. |
| 5,319,355 | A | 6/1994 | Russek |
| 5,319,363 | A | 6/1994 | Welch et al. |
| 5,330,634 | A | 7/1994 | Wong et al. |
| 5,338,157 | A | 8/1994 | Blomquist |
| 5,341,476 | A | 8/1994 | Lowell |
| 5,364,346 | A | 11/1994 | Schrezenmeir |
| 5,366,346 | A | 11/1994 | Danby |
| 5,368,562 | A | 11/1994 | Blomquist et al. |
| 5,373,454 | A | 12/1994 | Kanda et al. |
| 5,376,070 | A | 12/1994 | Purvis et al. |
| 5,378,231 | A | 1/1995 | Johnson et al. |
| 5,389,071 | A | 2/1995 | Kawahara et al. |
| 5,389,078 | A | 2/1995 | Zalesky et al. |
| 5,417,222 | A | 5/1995 | Dempsey et al. |
| 5,423,748 | A | 6/1995 | Uhala |
| 5,429,602 | A | 7/1995 | Hauser |
| 5,431,627 | A | 7/1995 | Pastrone et al. |
| 5,432,777 | A | 7/1995 | Le Boudec et al. |
| 5,445,621 | A | 8/1995 | Poli et al. |
| 5,447,164 | A | 9/1995 | Shaya et al. |
| 5,455,851 | A | 10/1995 | Chaco et al. |
| 5,461,365 | A | 10/1995 | Schlager et al. |
| 5,464,392 | A | 11/1995 | Epstein et al. |
| 5,465,082 | A | 11/1995 | Chaco |
| 5,485,408 | A | 1/1996 | Blomquist |
| 5,486,286 | A | 1/1996 | Peterson et al. |
| 5,493,430 | A | 2/1996 | Lu et al. |
| 5,496,273 | A | 3/1996 | Pastrone et al. |
| 5,505,828 | A | 4/1996 | Wong et al. |
| 5,507,288 | A | 4/1996 | Bocker et al. |
| 5,507,786 | A | 4/1996 | Morgan et al. |
| 5,508,499 | A | 4/1996 | Ferrario |
| 5,515,713 | A | 5/1996 | Saugues et al. |
| 5,520,637 | A | 5/1996 | Pager et al. |
| 5,522,798 | A | 6/1996 | Johnson et al. |
| 5,547,470 | A | 8/1996 | Johnson et al. |
| 5,554,013 | A | 9/1996 | Owens et al. |
| 5,562,615 | A | 10/1996 | Nassif |
| 5,577,169 | A | 11/1996 | Prezioso |
| 5,582,323 | A | 12/1996 | Kurtenbach |
| 5,582,593 | A | 12/1996 | Hultman |
| 5,594,786 | A | 1/1997 | Chaco et al. |
| 5,598,519 | A | 1/1997 | Narayanan |
| 5,620,608 | A | 4/1997 | Rosa et al. |
| 5,630,710 | A | 5/1997 | Tune et al. |
| 5,636,044 | A | 6/1997 | Yuan et al. |
| 5,643,212 | A | 7/1997 | Coutre et al. |
| 5,651,775 | A | 7/1997 | Walker et al. |
| 5,658,131 | A | 8/1997 | Aoki et al. |
| 5,658,250 | A | 8/1997 | Blomquist et al. |
| 5,665,065 | A | 9/1997 | Colman et al. |

(56) References Cited

U.S. PATENT DOCUMENTS

| | | | |
|---|---|---|---|
| 5,669,877 | A | 9/1997 | Blomquist |
| 5,672,154 | A | 9/1997 | Sillén et al. |
| 5,681,285 | A * | 10/1997 | Ford ...................... G16H 40/40 |
| | | | 604/67 |
| 5,685,844 | A | 11/1997 | Marttila |
| 5,687,717 | A | 11/1997 | Halpern et al. |
| 5,689,229 | A | 11/1997 | Chaco et al. |
| 5,697,899 | A | 12/1997 | Hillman et al. |
| 5,699,509 | A | 12/1997 | Gary et al. |
| 5,708,714 | A | 1/1998 | Lopez et al. |
| 5,713,350 | A | 2/1998 | Yokota et al. |
| 5,713,856 | A | 2/1998 | Eggers et al. |
| 5,718,562 | A | 2/1998 | Lawless et al. |
| 5,719,761 | A | 2/1998 | Gatti et al. |
| 5,733,259 | A | 3/1998 | Valcke et al. |
| 5,738,102 | A | 4/1998 | Lemelson |
| 5,744,027 | A | 4/1998 | Connell et al. |
| 5,752,621 | A | 5/1998 | Passamante |
| 5,754,111 | A | 5/1998 | Garcia |
| 5,764,034 | A | 6/1998 | Bowman et al. |
| 5,764,159 | A | 6/1998 | Neftel et al. |
| 5,772,635 | A | 6/1998 | Dastur et al. |
| 5,774,865 | A | 6/1998 | Glynn |
| 5,778,256 | A | 7/1998 | Darbee |
| 5,778,345 | A | 7/1998 | McCartney |
| 5,781,442 | A | 7/1998 | Engleson et al. |
| 5,782,805 | A | 7/1998 | Meinzer et al. |
| 5,788,669 | A | 8/1998 | Peterson |
| 5,797,515 | A | 8/1998 | Liff et al. |
| 5,800,387 | A | 9/1998 | Duffy et al. |
| 5,814,015 | A | 9/1998 | Gargano et al. |
| 5,822,544 | A | 10/1998 | Chaco et al. |
| 5,822,715 | A | 10/1998 | Worthington et al. |
| 5,827,179 | A | 10/1998 | Lichter et al. |
| 5,832,448 | A | 11/1998 | Brown |
| 5,836,910 | A | 11/1998 | Duffy et al. |
| 5,850,344 | A | 12/1998 | Conkright |
| 5,867,821 | A | 2/1999 | Ballantyne et al. |
| 5,870,733 | A | 2/1999 | Bass et al. |
| 5,871,465 | A | 2/1999 | Vasko |
| 5,873,731 | A | 2/1999 | Predergast |
| 5,885,245 | A | 3/1999 | Lynch et al. |
| 5,897,493 | A | 4/1999 | Brown |
| 5,897,498 | A | 4/1999 | Canfield, II et al. |
| 5,910,252 | A | 6/1999 | Truitt et al. |
| 5,912,818 | A | 6/1999 | McGrady et al. |
| 5,915,240 | A | 6/1999 | Karpf |
| 5,920,054 | A | 7/1999 | Uber, III |
| 5,920,263 | A | 7/1999 | Huttenhoff et al. |
| 5,924,074 | A | 7/1999 | Evans |
| 5,931,764 | A | 8/1999 | Freeman et al. |
| 5,935,099 | A | 8/1999 | Peterson et al. |
| 5,935,106 | A | 8/1999 | Olsen |
| 5,941,846 | A | 8/1999 | Duffy et al. |
| 5,956,501 | A | 9/1999 | Brown |
| 5,957,885 | A | 9/1999 | Bollish et al. |
| 5,960,085 | A | 9/1999 | de la Huerga |
| 5,961,448 | A | 10/1999 | Swenson et al. |
| 5,967,559 | A | 10/1999 | Abramowitz |
| 5,971,594 | A | 10/1999 | Sahai et al. |
| 5,975,081 | A | 11/1999 | Hood et al. |
| 5,990,838 | A | 11/1999 | Burns et al. |
| 5,997,476 | A | 12/1999 | Brown |
| 6,000,828 | A | 12/1999 | Leet |
| 6,003,006 | A | 12/1999 | Colella et al. |
| 6,012,034 | A | 1/2000 | Hamparian et al. |
| 6,017,318 | A | 1/2000 | Gauthier et al. |
| 6,021,392 | A | 2/2000 | Lester et al. |
| 6,024,539 | A | 2/2000 | Blomquist |
| 6,024,699 | A | 2/2000 | Surwit et al. |
| 6,032,155 | A | 2/2000 | de la Huerga |
| 6,032,676 | A | 3/2000 | Moore |
| 6,039,251 | A | 3/2000 | Holowko et al. |
| 6,070,761 | A | 6/2000 | Bloom et al. |
| 6,073,106 | A | 6/2000 | Rozen et al. |
| 6,104,295 | A | 8/2000 | Gaisser et al. |
| 6,112,182 | A | 8/2000 | Akers et al. |
| 6,112,323 | A | 8/2000 | Meizlik et al. |
| RE36,871 | E | 9/2000 | Epstein et al. |
| 6,115,365 | A | 9/2000 | Newberg |
| 6,115,390 | A | 9/2000 | Chuah |
| 6,122,536 | A | 9/2000 | Sun et al. |
| 6,126,637 | A | 10/2000 | Kriesel et al. |
| 6,135,949 | A | 10/2000 | Russo et al. |
| 6,150,942 | A | 11/2000 | O'Brien |
| 6,151,643 | A | 11/2000 | Cheng et al. |
| 6,157,914 | A | 12/2000 | Seto et al. |
| 6,159,147 | A | 12/2000 | Lichter et al. |
| 6,167,567 | A | 12/2000 | Chiles et al. |
| 6,182,667 | B1 | 2/2001 | Hanks et al. |
| 6,189,105 | B1 | 2/2001 | Lopes |
| 6,195,589 | B1 | 2/2001 | Ketcham |
| 6,208,974 | B1 | 3/2001 | Campbell et al. |
| 6,222,323 | B1 | 4/2001 | Yamashita et al. |
| 6,223,440 | B1 | 5/2001 | Rashman |
| 6,226,277 | B1 | 5/2001 | Chuah |
| 6,227,371 | B1 | 5/2001 | Song |
| 6,234,176 | B1 | 5/2001 | Domae et al. |
| 6,241,704 | B1 | 6/2001 | Peterson et al. |
| 6,248,067 | B1 | 6/2001 | Causey, III et al. |
| 6,249,705 | B1 | 6/2001 | Snell |
| 6,257,265 | B1 | 7/2001 | Brunner et al. |
| 6,259,355 | B1 | 7/2001 | Chaco et al. |
| 6,269,340 | B1 | 7/2001 | Ford et al. |
| 6,270,455 | B1 | 8/2001 | Brown |
| 6,271,813 | B1 | 8/2001 | Palalau |
| 6,277,072 | B1 | 8/2001 | Bardy |
| 6,280,380 | B1 | 8/2001 | Bardy |
| 6,283,761 | B1 | 9/2001 | Joao |
| 6,285,665 | B1 | 9/2001 | Chuah |
| 6,292,860 | B1 | 9/2001 | Cochcroft, Jr. |
| 6,312,378 | B1 | 11/2001 | Bardy |
| 6,327,254 | B1 | 12/2001 | Chuah |
| 6,330,008 | B1 | 12/2001 | Razdow et al. |
| 6,339,718 | B1 | 1/2002 | Zatezalo et al. |
| 6,346,886 | B1 | 2/2002 | de la Huerga |
| 6,363,282 | B1 | 3/2002 | Nichols et al. |
| 6,371,719 | B1 | 4/2002 | Hildebrandt |
| 6,377,548 | B1 | 4/2002 | Chuah |
| 6,388,951 | B1 | 5/2002 | Matsumoto et al. |
| 6,406,426 | B1 | 6/2002 | Reuss et al. |
| 6,408,330 | B1 | 6/2002 | de la Huerga |
| 6,418,334 | B1 | 7/2002 | Unger et al. |
| 6,427,088 | B1 | 7/2002 | Bowman et al. |
| 6,428,483 | B1 | 8/2002 | Carlebach |
| 6,442,432 | B2 | 8/2002 | Lee |
| 6,469,991 | B1 | 10/2002 | Chuah |
| 6,475,180 | B2 | 11/2002 | Peterson et al. |
| 6,482,158 | B2 | 11/2002 | Mault |
| 6,485,418 | B2 | 11/2002 | Yasushi et al. |
| 6,494,694 | B2 | 12/2002 | Lawless et al. |
| 6,494,831 | B1 | 12/2002 | Koritzinsky |
| 6,497,680 | B1 | 12/2002 | Holst et al. |
| 6,514,460 | B1 | 2/2003 | Fendrock |
| 6,517,482 | B1 | 2/2003 | Eiden et al. |
| 6,519,569 | B1 | 2/2003 | White et al. |
| 6,520,930 | B2 | 2/2003 | Critchlow et al. |
| 6,540,672 | B1 | 4/2003 | Simonsen et al. |
| 6,542,902 | B2 | 4/2003 | Dulong et al. |
| 6,544,212 | B2 | 4/2003 | Galley et al. |
| 6,544,228 | B1 | 4/2003 | Heitmeier |
| 6,546,350 | B1 | 4/2003 | Hartmann et al. |
| 6,551,276 | B1 | 4/2003 | Mann et al. |
| 6,554,798 | B1 | 4/2003 | Mann et al. |
| 6,558,320 | B1 | 5/2003 | Causey et al. |
| 6,558,351 | B1 | 5/2003 | Steil et al. |
| 6,565,509 | B1 | 5/2003 | Say et al. |
| 6,567,416 | B1 | 5/2003 | Chuah |
| 6,571,294 | B2 | 5/2003 | Simmon et al. |
| 6,572,542 | B1 | 6/2003 | Houben et al. |
| 6,572,545 | B2 | 6/2003 | Knobbe et al. |
| 6,578,002 | B1 | 6/2003 | Derzay et al. |
| 6,581,117 | B1 | 6/2003 | Klein et al. |
| 6,587,034 | B1 | 7/2003 | Heiman et al. |

(56)                  References Cited

U.S. PATENT DOCUMENTS

| | | | |
|---|---|---|---|
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Cmkovich et al. |
| 6,780,156 B2 | 8/2004 | Haueter et al. |
| 6,790,198 B1 | 9/2004 | White et al. |
| 6,792,470 B2 | 9/2004 | Hakenberg et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,928,490 B1 | 8/2005 | Bucholz et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B2 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,016,752 B1 | 3/2006 | Ruben et al. |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,114,002 B1 | 9/2006 | Okumura et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,158,030 B2 | 1/2007 | Chung |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | Mckeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |
| 7,399,277 B2 | 7/2008 | Saidara et al. |
| 7,402,153 B2 | 7/2008 | Steil et al. |

(56) References Cited

U.S. PATENT DOCUMENTS

| | | |
|---|---|---|
| 7,420,472 B2 | 9/2008 | Tran |
| 7,432,807 B2 | 10/2008 | Schmitt |
| 7,436,454 B2 | 10/2008 | Yamaguchi et al. |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,469,213 B1 | 12/2008 | Rao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal et al. |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,788,369 B2 | 8/2010 | McAllen et al. |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,864,771 B2 | 1/2011 | Tavares et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,976,508 B2 | 7/2011 | Hoag |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,075,514 B2 | 12/2011 | Butterfield et al. |
| 8,078,983 B2 | 12/2011 | Davis et al. |
| 8,082,018 B2 | 12/2011 | Duchon et al. |
| 8,082,312 B2 | 12/2011 | Chan et al. |
| 8,095,692 B2 | 1/2012 | Mehta et al. |
| 8,126,730 B2 | 2/2012 | Dicks et al. |
| 8,147,448 B2 | 4/2012 | Sundar et al. |
| 8,149,131 B2 | 4/2012 | Blomquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,312,272 B1 | 11/2012 | Serenyl et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,398,592 B2 | 3/2013 | Leibner-Druska |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,472,630 B2 | 6/2013 | Konrad et al. |
| 8,480,648 B2 | 7/2013 | Burnett et al. |
| 8,486,019 B2 | 7/2013 | White et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,567,681 B2 | 10/2013 | Borges et al. |
| 8,577,692 B2 | 11/2013 | Silkaitis et al. |
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,667,293 B2 | 3/2014 | Birtwhistle et al. |
| 8,687,811 B2 | 4/2014 | Nierzwick et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,886,316 B1 | 11/2014 | Juels |
| 8,922,330 B2 | 12/2014 | Moberg et al. |
| 8,936,565 B2 | 1/2015 | Chawla |
| 8,945,043 B2 | 2/2015 | Lee et al. |
| 8,952,794 B2 | 2/2015 | Blomquist et al. |
| 8,959,617 B2 | 2/2015 | Newlin et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,077,544 B2 | 7/2015 | Baker et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,292,692 B2 | 3/2016 | Wallrabenstein |
| 9,302,035 B2 | 4/2016 | Marseille et al. |
| 9,313,154 B1 | 4/2016 | Son |
| 9,381,296 B2 | 7/2016 | Arrizza et al. |

(56) References Cited

U.S. PATENT DOCUMENTS

| | | | |
|---|---|---|---|
| 9,393,362 | B2 | 7/2016 | Cozmi et al. |
| 9,430,655 | B1 | 8/2016 | Stockton et al. |
| 9,438,580 | B2 | 9/2016 | Kupper |
| 9,483,615 | B2 | 11/2016 | Roberts |
| 9,498,583 | B2 | 11/2016 | Sur et al. |
| 9,539,383 | B2 | 1/2017 | Kohlbrecher |
| 9,572,923 | B2 | 2/2017 | Howard et al. |
| 9,594,875 | B2 | 3/2017 | Arrizza et al. |
| 9,604,000 | B2 | 3/2017 | Wehba et al. |
| 9,641,432 | B2 | 5/2017 | Jha et al. |
| 9,649,431 | B2 | 5/2017 | Gray et al. |
| 9,662,436 | B2 | 5/2017 | Belkin et al. |
| 9,690,909 | B2 | 6/2017 | Stewart et al. |
| 9,707,341 | B2 | 7/2017 | Dumas, III et al. |
| 9,717,845 | B2 | 8/2017 | Istoc |
| 9,724,470 | B2 | 8/2017 | Day et al. |
| 9,729,330 | B2 | 8/2017 | Verma |
| 9,764,082 | B2 | 9/2017 | Day et al. |
| 9,886,550 | B2 | 2/2018 | Lee et al. |
| 9,943,269 | B2 | 4/2018 | Muhsin et al. |
| 9,967,739 | B2 | 5/2018 | Proennecke et al. |
| 9,971,871 | B2 | 5/2018 | Arrizza et al. |
| 9,995,611 | B2 | 6/2018 | Ruchti et al. |
| 10,022,498 | B2 | 7/2018 | Ruchti et al. |
| 10,042,986 | B2 | 8/2018 | Ruchti et al. |
| 10,046,112 | B2 | 8/2018 | Oruklu et al. |
| 10,166,328 | B2 | 1/2019 | Oruklu et al. |
| 10,173,008 | B2 | 1/2019 | Simpson et al. |
| 10,188,849 | B2 | 1/2019 | Fangrow |
| 10,233,179 | B2 | 3/2019 | Ng et al. |
| 10,238,799 | B2 | 3/2019 | Kohlbrecher |
| 10,238,801 | B2 | 3/2019 | Wehba et al. |
| 10,242,060 | B2 | 3/2019 | Butler et al. |
| 10,300,194 | B2 | 5/2019 | Day et al. |
| 10,311,972 | B2 | 6/2019 | Kohlbrecher et al. |
| 10,314,974 | B2 | 6/2019 | Day et al. |
| 10,333,843 | B2 | 6/2019 | Jha et al. |
| 10,341,866 | B1 | 7/2019 | Spencer et al. |
| 10,409,995 | B1 | 9/2019 | Wasiq |
| 10,430,761 | B2 | 10/2019 | Hume et al. |
| 10,434,246 | B2 | 10/2019 | Silkaitis et al. |
| 10,438,001 | B1 | 10/2019 | Hariprasad |
| 10,452,842 | B2 | 10/2019 | Dhondse |
| 10,453,157 | B2 | 10/2019 | Kamen et al. |
| 10,463,788 | B2 | 11/2019 | Day |
| 10,516,536 | B2 | 12/2019 | Rommel |
| 10,617,815 | B2 | 4/2020 | Day et al. |
| 10,646,651 | B2 | 5/2020 | Day et al. |
| 10,681,207 | B1 | 6/2020 | Johnson et al. |
| 10,692,595 | B2 | 6/2020 | Xavier et al. |
| 10,728,262 | B1 | 7/2020 | Vaswani |
| 10,740,436 | B2 | 8/2020 | Moskal et al. |
| 10,741,280 | B2 | 8/2020 | Xavier et al. |
| 10,757,219 | B2 | 8/2020 | Moskal |
| 10,765,799 | B2 | 9/2020 | Belkin et al. |
| 10,799,632 | B2 | 10/2020 | Kohlbrecher |
| 10,812,380 | B2 | 10/2020 | Jha et al. |
| 10,861,592 | B2 | 12/2020 | Xavier et al. |
| 10,898,641 | B2 | 1/2021 | Day et al. |
| 10,950,339 | B2 | 3/2021 | Xavier et al. |
| 10,964,428 | B2 | 3/2021 | Xavier et al. |
| 11,013,861 | B2 | 5/2021 | Wehba et al. |
| 11,037,668 | B2 | 6/2021 | Ruchti et al. |
| 11,052,193 | B2 | 7/2021 | Day et al. |
| 11,139,058 | B2 | 10/2021 | Xavier et al. |
| 11,151,290 | B2 | 10/2021 | Karakoyunlu et al. |
| 11,152,108 | B2 | 10/2021 | Xavier et al. |
| 11,152,109 | B2 | 10/2021 | Xavier et al. |
| 11,152,110 | B2 | 10/2021 | Xavier et al. |
| 11,194,810 | B2 | 12/2021 | Butler et al. |
| 11,235,100 | B2 | 2/2022 | Howard et al. |
| 11,289,183 | B2 | 3/2022 | Kohlbrecher |
| 11,309,070 | B2 | 4/2022 | Xavier et al. |
| 11,328,804 | B2 | 5/2022 | Xavier et al. |
| 11,328,805 | B2 | 5/2022 | Xavier et al. |
| 11,373,753 | B2 | 6/2022 | Xavier et al. |
| 11,437,132 | B2 | 9/2022 | Xavier et al. |
| 11,470,000 | B2 | 10/2022 | Jha et al. |
| 11,483,402 | B2 | 10/2022 | Xavier et al. |
| 11,483,403 | B2 | 10/2022 | Xavier et al. |
| 11,501,877 | B2 | 11/2022 | Kohlbrecher et al. |
| 11,571,508 | B2 | 2/2023 | Jacobson et al. |
| 11,574,721 | B2 | 2/2023 | Kohlbrecher |
| 11,574,737 | B2 | 2/2023 | Dharwad et al. |
| 11,587,669 | B2 | 2/2023 | Xavier et al. |
| 11,590,057 | B2 | 2/2023 | Tagliamento et al. |
| 11,594,326 | B2 | 2/2023 | Xavier et al. |
| 11,605,468 | B2 | 3/2023 | Jacobson et al. |
| 11,626,205 | B2 | 4/2023 | Arrizza et al. |
| 11,628,246 | B2 | 4/2023 | Day et al. |
| 11,628,254 | B2 | 4/2023 | Day et al. |
| 11,654,237 | B2 | 5/2023 | Wehba et al. |
| 11,670,416 | B2 | 6/2023 | Xavier et al. |
| 11,763,927 | B2 | 9/2023 | Ruchti et al. |
| 11,783,935 | B2 | 10/2023 | Xavier et al. |
| 11,881,297 | B2 | 1/2024 | Xavier et al. |
| 11,923,076 | B2 | 3/2024 | Xavier et al. |
| 11,986,623 | B2 | 5/2024 | Jacobson et al. |
| 11,996,188 | B2 | 5/2024 | Arrizza et al. |
| 12,002,562 | B2 | 6/2024 | Kohlbrecher |
| 12,036,390 | B2 | 7/2024 | Wehba et al. |
| 12,040,068 | B2 | 7/2024 | Xavier et al. |
| 12,042,623 | B2 | 7/2024 | Day et al. |
| 12,042,631 | B2 | 7/2024 | Day et al. |
| 12,046,361 | B2 | 7/2024 | Xavier et al. |
| 12,047,292 | B2 | 7/2024 | Jha et al. |
| 12,097,351 | B2 | 9/2024 | Belkin et al. |
| 12,130,910 | B2 | 10/2024 | Vivek et al. |
| 12,142,370 | B2 | 11/2024 | Xavier et al. |
| 12,205,702 | B2 | 1/2025 | Xavier et al. |
| 12,337,142 | B2 | 6/2025 | Wehba et al. |
| 2001/0016056 | A1 | 8/2001 | Westphal et al. |
| 2001/0029178 | A1 | 10/2001 | Criss et al. |
| 2001/0031944 | A1 | 10/2001 | Peterson et al. |
| 2001/0032099 | A1 | 10/2001 | Joao |
| 2001/0037060 | A1 | 11/2001 | Thompson et al. |
| 2001/0044731 | A1 | 11/2001 | Coffman et al. |
| 2001/0048027 | A1 | 12/2001 | Walsh |
| 2001/0051787 | A1 | 12/2001 | Haller et al. |
| 2001/0056358 | A1 | 12/2001 | Dulong et al. |
| 2002/0010595 | A1 | 1/2002 | Kapp |
| 2002/0013551 | A1 | 1/2002 | Zaitsu et al. |
| 2002/0013723 | A1 | 1/2002 | Mise |
| 2002/0015018 | A1 | 2/2002 | Shimazu et al. |
| 2002/0019584 | A1 | 2/2002 | Schulze et al. |
| 2002/0021700 | A1 | 2/2002 | Hata et al. |
| 2002/0026103 | A1 | 2/2002 | Norris et al. |
| 2002/0029776 | A1 | 3/2002 | Blomquist |
| 2002/0032583 | A1 | 3/2002 | Joao |
| 2002/0040208 | A1 | 4/2002 | Flaherty et al. |
| 2002/0040282 | A1 | 4/2002 | Bailey et al. |
| 2002/0044043 | A1 | 4/2002 | Chaco et al. |
| 2002/0044059 | A1 | 4/2002 | Reeder et al. |
| 2002/0082728 | A1 | 6/2002 | Mueller et al. |
| 2002/0087115 | A1 | 7/2002 | Hartlaub |
| 2002/0087116 | A1 | 7/2002 | Hartlaub |
| 2002/0095486 | A1 | 7/2002 | Bahl |
| 2002/0103675 | A1 | 8/2002 | Vanelli |
| 2002/0123905 | A1 | 9/2002 | Goodroe et al. |
| 2002/0143580 | A1 | 10/2002 | Bristol et al. |
| 2002/0152239 | A1 | 10/2002 | Bautista-Lloyd et al. |
| 2002/0154600 | A1 | 10/2002 | Ido et al. |
| 2002/0173702 | A1 | 11/2002 | Lebel et al. |
| 2002/0173875 | A1 | 11/2002 | Wallace et al. |
| 2002/0193679 | A1 | 12/2002 | Malave et al. |
| 2002/0194329 | A1 | 12/2002 | Alling |
| 2003/0009244 | A1 | 1/2003 | Engleson |
| 2003/0013959 | A1 | 1/2003 | Grunwald et al. |
| 2003/0014222 | A1 | 1/2003 | Klass et al. |
| 2003/0014817 | A1 | 1/2003 | Gallant et al. |
| 2003/0025602 | A1 | 2/2003 | Medema et al. |
| 2003/0028082 | A1 | 2/2003 | Thompson |
| 2003/0036683 | A1 | 2/2003 | Kehr et al. |
| 2003/0036744 | A1 | 2/2003 | Struys et al. |

(56) References Cited

U.S. PATENT DOCUMENTS

| | | |
|---|---|---|
| 2003/0047126 A1 | 3/2003 | Tomaschko |
| 2003/0047600 A1 | 3/2003 | Nakanishi et al. |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0105389 A1 | 6/2003 | Noonan et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0216831 A1 | 11/2003 | Hart et al. |
| 2003/0217962 A1 | 11/2003 | Childers et al. |
| 2004/0008123 A1 | 1/2004 | Carrender et al. |
| 2004/0010786 A1 | 1/2004 | Cool et al. |
| 2004/0015132 A1 | 1/2004 | Brown |
| 2004/0019464 A1 | 1/2004 | Martucci et al. |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073161 A1 | 4/2004 | Tachibana |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0085186 A1 | 5/2004 | Eveland et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox et al. |
| 2005/0086072 A1 | 4/2005 | Fox |
| 2005/0088704 A1 | 4/2005 | Vaschillo et al. |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | McLaughlin |
| 2005/0138428 A1 | 6/2005 | McAllen et al. |
| 2005/0144043 A1* | 6/2005 | Holland ............ G16H 70/40 |
| | | 705/3 |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |

(56)            References Cited

U.S. PATENT DOCUMENTS

| | | |
|---|---|---|
| 2006/0074920 A1 | 4/2006 | Wefers et al. |
| 2006/0079831 A1 | 4/2006 | Gilbert |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0236373 A1 | 10/2006 | Graves et al. |
| 2006/0247606 A1 | 11/2006 | Batch |
| 2006/0253554 A1 | 11/2006 | Uwais |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0021715 A1 | 1/2007 | Kohlbrenner et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0073822 A1 | 3/2007 | Bennett et al. |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0229249 A1 | 10/2007 | McNeal et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0240215 A1 | 10/2007 | Flores |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0001771 A1 | 1/2008 | Faoro et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0086088 A1 | 4/2008 | Malcolm |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0097552 A1 | 4/2008 | Dicks et al. |
| 2008/0126969 A1 | 5/2008 | Blomquist |
| 2008/0139907 A1 | 6/2008 | Rao et al. |
| 2008/0148047 A1 | 6/2008 | Appenzeller et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0301298 A1 | 12/2008 | Bernardi et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0036750 A1 | 2/2009 | Weinstein et al. |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0063187 A1 | 3/2009 | Johnson et al. |
| 2009/0069785 A1 | 3/2009 | Miller et al. |
| 2009/0099866 A1 | 4/2009 | Newman |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0156991 A1 | 6/2009 | Roberts |
| 2009/0157695 A1 | 6/2009 | Roberts |

(56) References Cited

U.S. PATENT DOCUMENTS

| | | |
|---|---|---|
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Blomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0008377 A1 | 1/2010 | Hasti et al. |
| 2010/0022988 A1 | 1/2010 | Wochner |
| 2010/0036310 A1 | 2/2010 | Hillman |
| 2010/0056992 A1 | 3/2010 | Hayter |
| 2010/0083060 A1 | 4/2010 | Rahman |
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0028885 A1 | 2/2011 | Eggers et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0106318 A1 | 5/2011 | Ledford et al. |
| 2011/0125095 A1 | 5/2011 | Lebel et al. |
| 2011/0138185 A1 | 6/2011 | Ju et al. |
| 2011/0166628 A1 | 7/2011 | Jain |
| 2011/0175728 A1 | 7/2011 | Baker, Jr. |
| 2011/0178462 A1 | 7/2011 | Moberg et al. |
| 2011/0185010 A1 | 7/2011 | Shatsky et al. |
| 2011/0196748 A1 | 8/2011 | Caron et al. |
| 2011/0231216 A1 | 9/2011 | Fyke et al. |
| 2011/0252230 A1 | 10/2011 | Segre et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289162 A1 | 11/2011 | Furlong |
| 2011/0289314 A1 | 11/2011 | Whitcomb |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0036550 A1 | 2/2012 | Rodriguez |
| 2012/0066501 A1 | 3/2012 | Xiong |
| 2012/0070045 A1 | 3/2012 | Vesper et al. |
| 2012/0079084 A1 | 3/2012 | Forssell et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0172802 A1 | 7/2012 | Blomquist et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0260012 A1 | 10/2012 | Gao-Saari et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2012/0330380 A1 | 12/2012 | Corndorf |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0091350 A1 | 4/2013 | Gluck |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0114594 A1 | 5/2013 | Van Zijst |
| 2013/0116578 A1 | 5/2013 | An |
| 2013/0133083 A1 | 5/2013 | Kurumai |
| 2013/0138452 A1 | 5/2013 | Cork et al. |
| 2013/0144206 A1 | 6/2013 | Lee et al. |
| 2013/0150824 A1 | 6/2013 | Estes et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0039446 A1 | 2/2014 | Day |

(56) References Cited

U.S. PATENT DOCUMENTS

| 2014/0108783 A1 | 4/2014 | Suzuki |
| 2014/0142540 A1 | 5/2014 | Imhof |
| 2014/0142963 A1 | 5/2014 | Hill et al. |
| 2014/0163517 A1 | 6/2014 | Finan et al. |
| 2014/0172994 A1 | 6/2014 | Raumann et al. |
| 2014/0180711 A1 | 6/2014 | Kamen et al. |
| 2014/0197950 A1 | 7/2014 | Shupp et al. |
| 2014/0215490 A1 | 7/2014 | Mathur et al. |
| 2014/0257251 A1 | 9/2014 | Bush et al. |
| 2014/0266790 A1 | 9/2014 | Al-Ali et al. |
| 2014/0266794 A1 | 9/2014 | Brown et al. |
| 2014/0269643 A1 | 9/2014 | Sun |
| 2014/0276571 A1 | 9/2014 | Ludolph |
| 2014/0280522 A1 | 9/2014 | Watte |
| 2014/0288947 A1 | 9/2014 | Simpson et al. |
| 2014/0294177 A1 | 10/2014 | Shastry et al. |
| 2014/0297329 A1 | 10/2014 | Rock |
| 2014/0316819 A1 | 10/2014 | Dunsirn et al. |
| 2014/0318639 A1 | 10/2014 | Peret et al. |
| 2014/0350513 A1 | 11/2014 | Oruklu et al. |
| 2014/0358077 A1 | 12/2014 | Oruklu et al. |
| 2014/0366878 A1 | 12/2014 | Baron |
| 2014/0371543 A1 | 12/2014 | Steinhauer et al. |
| 2015/0005935 A1 | 1/2015 | Bae et al. |
| 2015/0006907 A1 | 1/2015 | Brouwer et al. |
| 2015/0045729 A1 | 2/2015 | Denzer et al. |
| 2015/0058044 A1 | 2/2015 | Butler et al. |
| 2015/0058960 A1 | 2/2015 | Schmoyer et al. |
| 2015/0066531 A1 | 3/2015 | Jacobson et al. |
| 2015/0081894 A1 | 3/2015 | Blomquist |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0134265 A1 | 5/2015 | Kohlbrecher et al. |
| 2015/0141955 A1 | 5/2015 | Ruchti et al. |
| 2015/0151051 A1 | 6/2015 | Tsoukalis |
| 2015/0161354 A1 | 6/2015 | Blomquist |
| 2015/0199192 A1 | 7/2015 | Borges et al. |
| 2015/0199485 A1 | 7/2015 | Borges et al. |
| 2015/0207626 A1 | 7/2015 | Neftel et al. |
| 2015/0220890 A1 | 8/2015 | Seshadri et al. |
| 2015/0230760 A1 | 8/2015 | Schneider |
| 2015/0281128 A1 | 10/2015 | Sindhu |
| 2015/0325064 A1 | 11/2015 | Downey |
| 2015/0328396 A1 | 11/2015 | Adams et al. |
| 2015/0352301 A1 | 12/2015 | Stedman et al. |
| 2015/0371004 A1 | 12/2015 | Jones |
| 2015/0379237 A1 | 12/2015 | Mills et al. |
| 2016/0001003 A1 | 1/2016 | Perazzo et al. |
| 2016/0006695 A1 | 1/2016 | Prodoehl et al. |
| 2016/0015885 A1 | 1/2016 | Pananen et al. |
| 2016/0034655 A1 | 2/2016 | Gray et al. |
| 2016/0045661 A1 | 2/2016 | Gray et al. |
| 2016/0051749 A1 | 2/2016 | Istoc |
| 2016/0051751 A1 | 2/2016 | Silkaitis et al. |
| 2016/0063471 A1 | 3/2016 | Kobres et al. |
| 2016/0103960 A1 | 4/2016 | Hume et al. |
| 2016/0158437 A1 | 6/2016 | Biasi et al. |
| 2016/0228633 A1 | 8/2016 | Welsch et al. |
| 2016/0241391 A1 | 8/2016 | Fenster |
| 2016/0277152 A1 | 9/2016 | Xiang et al. |
| 2016/0285876 A1 | 9/2016 | Perez et al. |
| 2016/0317742 A1 | 11/2016 | Gannon et al. |
| 2016/0350513 A1 | 12/2016 | Jacobson et al. |
| 2016/0378618 A1 | 12/2016 | Cmielowski |
| 2017/0034277 A1 | 2/2017 | Jackson et al. |
| 2017/0054563 A1 | 2/2017 | Verma |
| 2017/0063559 A1 | 3/2017 | Wallrabenstein |
| 2017/0099148 A1 | 4/2017 | Ochmanski et al. |
| 2017/0104645 A1 | 4/2017 | Wooton et al. |
| 2017/0111301 A1 | 4/2017 | Robinson |
| 2017/0134357 A1 | 5/2017 | Ohlsson |
| 2017/0140134 A1 | 5/2017 | Brough et al. |
| 2017/0146381 A1 | 5/2017 | Eckel et al. |
| 2017/0149567 A1 | 5/2017 | Moskal |
| 2017/0149929 A1 | 5/2017 | Moskal |
| 2017/0214762 A1 | 7/2017 | Swain et al. |
| 2017/0246388 A1 | 8/2017 | Kohlbrecher |
| 2017/0258401 A1 | 9/2017 | Volpe |
| 2017/0258986 A1 | 9/2017 | Tsoiukalis |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0319780 A1 | 11/2017 | Belkin et al. |
| 2017/0325091 A1 | 11/2017 | Freeman et al. |
| 2017/0331735 A1 | 11/2017 | Jha et al. |
| 2017/0331804 A1 | 11/2017 | Jellison et al. |
| 2017/0351841 A1 | 12/2017 | Moskal |
| 2018/0008772 A1 | 1/2018 | Wehba et al. |
| 2018/0028742 A1 | 2/2018 | Day et al. |
| 2018/0043094 A1 | 2/2018 | Day et al. |
| 2018/0063724 A1 | 3/2018 | Zhang et al. |
| 2018/0121613 A1 | 5/2018 | Connely, IV et al. |
| 2018/0122502 A1 | 5/2018 | Jones et al. |
| 2018/0126067 A1 | 5/2018 | Ledford et al. |
| 2018/0157821 A1 | 6/2018 | Fan |
| 2018/0181712 A1 | 6/2018 | Ensey et al. |
| 2018/0247712 A1 | 8/2018 | Muhsin et al. |
| 2018/0272117 A1 | 9/2018 | Fangrow |
| 2018/0278594 A1 | 9/2018 | Schiffman et al. |
| 2018/0317826 A1 | 11/2018 | Muhsin et al. |
| 2018/0322948 A1 | 11/2018 | Drost et al. |
| 2018/0359085 A1 | 12/2018 | Dervyn |
| 2019/0006044 A1 | 1/2019 | Brask |
| 2019/0030329 A1 | 1/2019 | Hannaman et al. |
| 2019/0036688 A1 | 1/2019 | Wasily et al. |
| 2019/0096518 A1 | 3/2019 | Pace |
| 2019/0116160 A1 | 4/2019 | Bhat et al. |
| 2019/0132196 A1 | 5/2019 | Trivedi et al. |
| 2019/0147998 A1 | 5/2019 | Ruchti et al. |
| 2019/0166501 A1 | 5/2019 | Debates et al. |
| 2019/0172590 A1 | 6/2019 | Vesto et al. |
| 2019/0182349 A1 | 6/2019 | Goel et al. |
| 2019/0207965 A1 | 7/2019 | Espinosa |
| 2019/0228863 A1 | 7/2019 | Dharwad et al. |
| 2019/0229982 A1 | 7/2019 | Ikuta et al. |
| 2019/0240405 A1 | 8/2019 | Wehba et al. |
| 2019/0243829 A1 | 8/2019 | Butler et al. |
| 2019/0244689 A1 | 8/2019 | Atkin |
| 2019/0244707 A1 | 8/2019 | Becker |
| 2019/0245942 A1 | 8/2019 | Moskal |
| 2019/0269852 A1 | 9/2019 | Kohlbrecher |
| 2019/0311803 A1 | 10/2019 | Kohlbrecher et al. |
| 2019/0348160 A1 | 11/2019 | Heavelyn et al. |
| 2019/0392929 A1 | 12/2019 | Gassman |
| 2020/0023127 A1 | 1/2020 | Simpson et al. |
| 2020/0027541 A1 | 1/2020 | Xavier et al. |
| 2020/0027542 A1 | 1/2020 | Xavier et al. |
| 2020/0027543 A1 | 1/2020 | Xavier et al. |
| 2020/0027548 A1 | 1/2020 | Xavier et al. |
| 2020/0027549 A1 | 1/2020 | Xavier et al. |
| 2020/0027550 A1 | 1/2020 | Xavier et al. |
| 2020/0027551 A1 | 1/2020 | Xavier et al. |
| 2020/0028837 A1 | 1/2020 | Xavier et al. |
| 2020/0028914 A1 | 1/2020 | Xavier et al. |
| 2020/0028929 A1 | 1/2020 | Xavier et al. |
| 2020/0035346 A1 | 1/2020 | Xavier et al. |
| 2020/0035355 A1 | 1/2020 | Xavier et al. |
| 2020/0054825 A1 | 2/2020 | Kamen et al. |
| 2020/0061291 A1 | 2/2020 | Day et al. |
| 2020/0118692 A1 | 4/2020 | Booker et al. |
| 2020/0153627 A1 | 5/2020 | Wentz |
| 2020/0206413 A1 | 7/2020 | Silkaitis et al. |
| 2020/0220865 A1 | 7/2020 | Finger et al. |
| 2020/0282139 A1 | 9/2020 | Susi |
| 2020/0334497 A1 | 10/2020 | Barrett et al. |
| 2020/0335194 A1 | 10/2020 | Jacobson et al. |
| 2020/0351376 A1 | 11/2020 | Moskal |
| 2020/0353167 A1 | 11/2020 | Vivek et al. |
| 2020/0353168 A1 | 11/2020 | Keenan et al. |
| 2021/0014259 A1 | 1/2021 | Harris et al. |
| 2021/0043296 A1 | 2/2021 | Xavier et al. |
| 2021/0045640 A1 | 2/2021 | Poltorak |
| 2021/0085855 A1 | 3/2021 | Belkin et al. |

(56)                References Cited

U.S. PATENT DOCUMENTS

| | | |
|---|---|---|
| 2021/0098107 A1 | 4/2021 | Xavier et al. |
| 2021/0105206 A1 | 4/2021 | Jha et al. |
| 2021/0136157 A1 | 5/2021 | Kauppila et al. |
| 2021/0252210 A1 | 8/2021 | Day et al. |
| 2021/0316072 A1 | 10/2021 | Wehba et al. |
| 2021/0358603 A1 | 11/2021 | Xavier et al. |
| 2021/0375421 A1 | 12/2021 | Ruchti et al. |
| 2021/0375438 A1 | 12/2021 | Xavier et al. |
| 2021/0409362 A1 | 12/2021 | Katis et al. |
| 2022/0023535 A1 | 1/2022 | Day |
| 2022/0037011 A1 | 2/2022 | Fryman |
| 2022/0037012 A1 | 2/2022 | Fryman |
| 2022/0051777 A1 | 2/2022 | Xavier et al. |
| 2022/0062541 A1 | 3/2022 | Kamen et al. |
| 2022/0129452 A1 | 4/2022 | Butler et al. |
| 2022/0139536 A1 | 5/2022 | Xavier et al. |
| 2022/0139537 A1 | 5/2022 | Xavier et al. |
| 2022/0139538 A1 | 5/2022 | Xavier et al. |
| 2022/0150307 A1 | 5/2022 | Walsh et al. |
| 2022/0165404 A1 | 5/2022 | Vivek et al. |
| 2022/0189605 A1 | 6/2022 | Kelly et al. |
| 2022/0223283 A1 | 7/2022 | Biasi et al. |
| 2022/0328175 A1 | 10/2022 | Arrizza et al. |
| 2022/0331513 A1 | 10/2022 | Howard et al. |
| 2022/0344023 A1 | 10/2022 | Xavier et al. |
| 2022/0375565 A1 | 11/2022 | Xavier et al. |
| 2022/0384059 A1 | 12/2022 | Xavier et al. |
| 2023/0009405 A1 | 1/2023 | Xavier et al. |
| 2023/0009417 A1 | 1/2023 | Xavier et al. |
| 2023/0139360 A1 | 5/2023 | Kohlbrecher et al. |
| 2023/0145267 A1 | 5/2023 | Xavier et al. |
| 2023/0147762 A1 | 5/2023 | Xavier et al. |
| 2023/0188465 A1 | 6/2023 | Jha et al. |
| 2023/0253108 A1 | 8/2023 | Dharwad et al. |
| 2023/0285660 A1 | 9/2023 | Day et al. |
| 2023/0320935 A1 | 10/2023 | Tagliamento |
| 2023/0321350 A1 | 10/2023 | Day |
| 2023/0321351 A1 | 10/2023 | Wehba et al. |
| 2023/0410989 A1 | 12/2023 | Xavier et al. |
| 2024/0038358 A1 | 2/2024 | Xavier et al. |
| 2024/0047035 A1 | 2/2024 | Ruchti et al. |
| 2024/0071606 A1 | 2/2024 | Xavier et al. |
| 2024/0071609 A1 | 2/2024 | Rohlwing |
| 2024/0293610 A1 | 9/2024 | Jacobson |
| 2024/0321441 A1 | 9/2024 | Rohlwing |
| 2024/0347161 A1 | 10/2024 | Kohlbrecher |
| 2024/0363236 A1 | 10/2024 | Arrizza et al. |
| 2024/0424197 A1 | 12/2024 | Day et al. |

FOREIGN PATENT DOCUMENTS

| | | |
|---|---|---|
| CA | 2 060 151 | 8/1997 |
| CA | 2 125 300 | 10/1999 |
| CA | 2 630 102 | 10/2008 |
| CA | 2 687 587 | 12/2008 |
| CA | 2 897 897 | 7/2014 |
| CA | 2 898 825 | 7/2014 |
| CA | 2 900 564 | 10/2014 |
| CA | 2 606 968 | 1/2020 |
| CN | 1759398 | 4/2006 |
| CN | 102521474 | 6/2012 |
| CN | 103816582 | 5/2014 |
| CN | 103920206 | 7/2014 |
| CN | 102300501 | 4/2015 |
| CN | 104487976 | 4/2015 |
| CN | 107810536 | 1/2023 |
| CO | 01110843 | 8/2003 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1 050 993 | 11/2000 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 1 487 171 | 7/2007 |
| EP | 1 933 497 | 6/2008 |
| EP | 2 026 223 | 2/2009 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| EP | 2 874 087 | 5/2015 |
| ES | 2 371 995 | 1/2012 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2003-308586 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| JP | 5647644 | 1/2015 |
| TW | 200426656 | 12/2004 |
| TW | 1631966 | 8/2018 |
| TW | M589351 | 1/2020 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 96/025963 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |

(56) References Cited

FOREIGN PATENT DOCUMENTS

| WO | WO 02/088875 | 11/2002 |
| WO | WO 03/006091 | 1/2003 |
| WO | WO 03/023551 | 3/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/057729 | 5/2008 |
| WO | WO 2008/059495 | 5/2008 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100557 | 6/2014 |
| WO | WO 2014/100687 | 6/2014 |
| WO | WO 2014/100736 | 6/2014 |
| WO | WO 2014/131729 | 9/2014 |
| WO | WO 2014/131730 | 9/2014 |
| WO | WO 2015/047595 | 4/2015 |
| WO | WO 2015/124569 | 8/2015 |
| WO | WO 2016/179389 | 11/2016 |
| WO | WO 2017/176928 | 10/2017 |
| WO | WO 2017/200989 | 11/2017 |
| WO | WO 2019/219290 | 11/2019 |
| WO | WO 00/003344 | 1/2020 |
| WO | WO 2020/227403 | 11/2020 |
| WO | WO 2021/201884 | 10/2021 |
| WO | WO 2022/006014 | 1/2022 |
| WO | WO 2022/051230 | 3/2022 |
| WO | WO 2023/159134 | 8/2023 |
| WO | WO 2024/196590 | 9/2024 |

OTHER PUBLICATIONS

Bellare et al., "Security Proofs for Identity-Based Identification and Signature Schemes", Lecture Notes in Computer Science, Jan. 2009, vol. 22, No. 1, pp. 18.

Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.

Doesburg et al., "Improved Usability of a Multi-Infusion Setup Using a Centralized Control Interface: A Task-Based Usability Test", Aug. 11, 2017, PLoS One, vol. 12, No. 8, pp. 10.

"Download", Free On-Line Dictionary of Computing, as archived Jun. 16, 2010 in 1 page, http://web.archive.org/web/20100616010314/https://foldoc.org/download.

Edworthy, Judy, "Medical Audible Alarms: A Review", Journal of the American Medical Informatics Association, vol. 20, No. 3, 2013, pp. 584-589.

Gutwin et al., "Gone But Not Forgotten: Designing for Disconnection in Synchronous Groupware", CSCW 2010, Feb. 6-10, 2010, Savannah, Georgia, USA., pp. 179-188.

Huang et al., "Secure Identity-Based Data Sharing and Profile Matching for Mobile Healthcare Social Networks in Cloud Computing", vol. 6, Jul. 2018, pp. 36584-36594.

Li et al., "Hijacking an Insulin Pump: Security Attacks and Defenses for a Diabetes Therapy System", 2011 IEEE 13th International Conference on e-Health Networking, Applications and Services, 2011, pp. 150-156.

"McKesson Automation and ALARIS Medical Systems Developing Point-of-Care Bar Coding Solution to Improve IV Medication Safety", PR Newswire, NY, Dec. 9, 2002, pp. 4.

Michienzi, Kelly, "Managing Drug Library Updates", Pharmacy Purchasing Products, https://www.pppmag.com/article/1061, Feb. 2012, vol. 9, pp. 22-23.

Nojoumian et al., "Social Secret Sharing in Cloud Computing Using a New Trust Function", 2012 Tenth Annual International Conference on Privacy, Security and Trust, pp. 161-167.

"SIGMA Spectrum: Operator's Manual", May 15, 2008, pp. 63. <https://usme.com/content/manuals/sigma-spectrum-operator-manual.pdf>.

Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.

"TCG TPM v2.0 Provisioning Guidance", Reference, Version 1, Revision 1, Mar. 15, 2017, pp. 1-43.

Yoo et al., "Code-Based Authentication Scheme for Lightweight Integrity Checking of Smart Vehicles", IEEE Access, 2018, vol. 6, pp. 46731-46741.

International Search Report and Written Opinion received in PCT Application No. PCT/IB2016/052822, dated Aug. 16, 2016 in 10 pages.

International Preliminary Report on Patentability and Written Opinion received in PCT Application No. PCT/IB2016/052822, dated Dec. 7, 2017 in 9 pages.

Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.

Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.

Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.

ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.

(56)          References Cited

OTHER PUBLICATIONS

Beard et al., "Total Quality Pain Management: History, Background, Resources", Abbott Laboratories, TQPM Survey History, available Feb. 2015 or earlier, pp. 1-3.
Bektas et al., "Bluetooth Communication Employing Antenna Diversity", Proceedings of Eight IEEE International Symposium on Computers and Communication, Jul. 2003, pp. 6.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Braun, "Infusomat® Space and Accessories", Instructions for Use, Nov. 2010, pp. 68. http://corp.bbraun.ee/Extranet/Infusionipumbad/Kasutusjuhendid/Vanad/Kasutusjuhend-Infusomat_Space(vers688J,inglise_k).pdf.
Brownlee, Seth, "Product Spotlight: The Plum A+ with Hospira MedNet Infusion System", PP&P Magazine, Dec. 2005, vol. 2, No. 7, pp. 2.
Cannon, MD et al., "Automated Heparin-Delivery System to Control Activated Partial Thromboplastin Time", Circulation, Feb. 16, 1999, vol. 99, pp. 751-756.
Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris_-_Service_Manual.pdf.
"CareAware@ Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.
"Computer Dictionary", Microsoft Press, Third Edition, Microsoft Press, 1997, pp. 430 & 506.
"Context-Free Grammar", Wikipedia.org, as last modified Mar. 5, 2010 in 11 pages, https://en.wikipedia.org/w/index.php/?title=Context-free_grammar&oldid=347915989.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
East PhD et al., "Digital Electronic Communication Between ICU Ventilators and Computers and Printers", Respiratory Care, Sep. 1992, vol. 37, No. 9, pp. 1113-1122.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Felleiter et al., "Data Processing in Prehospital Emergency Medicine", International journal of Clinical Monitoring and Computing, Feb. 1995, vol. 12, No. 1, pp. 37-41.
"File Verification", Wikipedia.org, as last modified Oct. 11, 2011 in 2 pages, https://en.wikipedia.org/w/index.php?title=File_verification&oldid=455048290.

Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gabel et al., "Camp: A Common API for Measuring Performance", 21st Large Installations System Administration Conference (LISA '07), 2007, pp. 49-61.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication Safety", Journal of Medical Library Association, Apr. 2005, vol. 93, No. 2, pp. 229-236.
Gardner, Ph.D. et al., "Real Time Data Acquisition: Recommendations for the Medical Information Bus (MIB)", 1992, pp. 813-817.
"General-Purpose Infusion Pumps", Health Devices, EXRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", http://www.trackingsystem.com/forbusinesses/corporate-trackingsystem/1098-gps-tracker-formedicalequipment.html, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "Pumpsim: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, www.hospira.com/products/gemstar_painmanagement.aspx, Jan. 28, 2010, pp. 1-2.
Introducing Abbott TQPM (Total Quality Pain Management), Abbott Laboratories, Abbott Park, IL, May 2000, pp. 1-4.
"Infusion Pump", Wikipedia.org, as last modified Mar. 27, 2014, in 3 pages, https://web.archive.org/web/20140703024932/https://en.wikipedia.org/wiki/Infusion_pump.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety in Veterans Administration Medical Centers", Journal of Healthcare Information Management, Dec. 6, 2004, vol. 16, No. 1, pp. 46-51.
Kent Displays, "Reflex™Electronic Skins", Product Brief 25127B, 2009, pp. 2.

(56) References Cited

OTHER PUBLICATIONS

Kent Displays, "Reflex Electronic Skins Engineering Evaluation Kit", 25136A, Mar. 10, 2009.

Lefkowitz et al., "A Trial of the Use of Bar Code Technology to Restructure a Drug Distribution and Administration System", Hospital Pharmacy, Mar. 31, 1991, vol. 26, No. 3, pp. 239-242.

Lenssen et al., "Bright Color Electronic Paper Technology and Applications", IDS '09 Publication EP1-2 (Phillips Research), 2009, pp. 529-532.

Leveson, Nancy, "Medical Devices: The Therac-25", Appendix A, University of Washington, 1995, pp. 49.

Linkens, D.A. "Computer Control for Patient Care", Computer Control of Real-Time Processes, IEE Control Engineering Series 41, 1990, Ch. 13, pp. 216-238.

Mako Hill et al., "The Official Ubuntu Book", Shoeisha Co., Ltd., 1st Edition, Jun. 11, 2007, pp. 115 to 125.

Marshall, et al., "New Microprocessor-Based Insulin Controller", IEEE Transactions on Biomedical Engineering, Nov. 1983, vol. BME-30, No. 11, pp. 689-695.

Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.

Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual_4000_40-5760-51A.pdf.

Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.

Micrel Medical Devices, "MP Daily +" http://web.archive.org/web/20130803235715/http://www.micrelmed.com/index.aspx?productid=9 as archived Aug. 3, 2013 in 1 page.

Moghissi, Etie, MD, FACP, FACE, "Hyperglycemia in Hospitalized Patients", A Supplement to ACP Hospitalist, Jun. 15, 2008, p. 32.

Murray, Jr. et al., "Automated Drug Identification System (during surgery)", IEEE Proceedings of Southeastcon '91, Apr. 7-10, 1991, pp. 265.

Nicholson et al., "Smart' Infusion Apparatus for Computation and Automated Delivery of Loading, Tapering, and Maintenance Infusion Regimens of Lidocaine, Procainamide, and Theophylline", Proceedings of the Seventh Annual Symposium on Computer Applications in Medical Care, Oct. 1983, pp. 212-213.

Nolan et al., "The P1073 Medical Information Bus Standard: Overview and Benefits for Clinical Users", 1990, pp. 216-219.

Omnilink Systems, Inc., "Portable Medical Equipment Tracking", http://www.omnilink.com/portablemedicalequipmenttracking/, Mar. 15, 2015, pp. 2.

O'Shea, Kristen L., "Infusion Management: Working Smarter, Not Harder", Hospital Pharmacy, Apr. 2013, vol. 48, No. 3, pp. S1-S14.

Package Management in Debian GNU/Linux, Debian GNU/Linux Expert Desktop Use Special, Giutsu-Hyohron Co., Ltd., First Edition, Sep. 25, 2004, pp. 183-185.

Passos et al., "Distributed Software Platform for Automation and Control of General Anaesthesia", Eighth International Symposium on Parallel and Distributed Computing, ISPDC '09, Jun. 30-Jul. 4, 2009, pp. 8.

Philips, "IntelliSpace Event Management and IntelliVue Patient Monitoring", Release 10, 2011, http://incenter.medical.philips.com/doclib/enc/fetch/2000/4504/577242/577243/577247/582646/583147/

8359175/Philips_Patient_Monitoring_and_IntelliSpace_Event_Management_Interoperability.pdf%3fnodeid%3d8508574%26vernum%3d-2, pp. 2.

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.

Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.

Ritchie et al., "A Microcomputer Based Controller for Neuromuscular Block During Surgery", Annals of Biomedical Engineering, Jan. 1985, vol. 13, No. 1, pp. 3-15.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sanders et al., "The Computer in a Programmable Implantable Medication System (PIMS)", Proceedings of the Annual Symposium on Computer Application in Medical Care, Nov. 2, 1982, pp. 682-685.

Schilling et al., "Optimizing Outcomes! Error Prevention and Evidence-Based Practice with IV Medications", A Pro-Ce Publication, Hospira, Inc., Feb. 6, 2012, pp. 56.

Schulze et al., "Advanced Sensors Technology Survey", Final Report, Feb. 10, 1992, pp. 161.

Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.

Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.

Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.

Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.

Sheppard, Louis, Ph.D., "Computer Control of the Infusion of Vasoactive Drugs", Annals of Biomedical Engineering, Jul. 1980, vol. 8, No. 4-6, pp. 431-444.

Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.

Sheppard, Louis, Ph.D., "The Computer in the Care of Critically Ill Patients", Proceedings of the IEEE, Sep. 1979, vol. 67, No. 9, pp. 1300-1306.

"Sigma Spectrum: Operator's Manual", Oct. 2009, pp. 72. http://static.medonecapital.com/manuals/userManuals/Sigma-Spectrum-Operator-Manual-October-2009.pdf.

Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.

Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasland.com/hpj4209-832.pdf.

Slack, W.V., "Information Technologies for Transforming Health Care", https://www.andrew.cmu.edu/course/90-853/medis.dir/otadocs.dir/03ch2.pdf, Ch. 2, 1995, pp. 29-78.

Smith, Joe, "Infusion Pump Informatics", CatalyzeCare: Transforming Healthcare, as printed May 12, 2011, pp. 2.

Sodders, Lisa, "VA Center Keeps Medicine in Right Hands", The Capital-Journal, Dec. 4, 1999, pp. 1-2.

"Software Versioning", Wikipedia.org, dated Oct. 16, 2011 in 11 pages, https://en.wikipedia.org/w/index.php?title=Software_versioning&oldid=455859110.

(56)  References Cited

OTHER PUBLICATIONS

Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
Sethia et al., "Security Framework for Portable NFC Mobile Based Health Record System", Oct. 2016, IEEE 12th International Conference on Wireless and Mobile Computing, Networking and Communications, pp. 1-8.
Murphy, Robert, "The Design of Safety-Critical Medical Infusion Devices", May 30, 2007, Doctor of Philosophy submission, pp. 317.
Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.
Cloudflare, "What Happens in a TLS Handshake? | SSL Handshake", as archived May 19, 2020, https://web.archive.org/web/20200519192121/https:/www.cloudflare.com/en-au/learning/ssl/what-happens-in-a-tls-handshake/, 4 pages.
Fan et al., "Smart Medication Delivery Systems: Infusion Pumps", Supplementary Report, Healthcare Human Factors, Feb. 26, 2010, pp. 94.
Stack Exchange, "Avoiding SSL handshake for each call", as archived Sep. 22, 2021, https://web.archive.org/web/20210922184153/https:/security.stackexchange.com/questions/56623/avoiding-ssl-handshake-for-each-call, 3 pages.

* cited by examiner

1

INFUSION PUMP SYSTEM AND METHOD WITH MULTIPLE DRUG LIBRARY EDITOR SOURCE CAPABILITY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to medical devices. More specifically, the invention relates to infusion pump systems and methods with multiple drug library editor source capability.

Description of the Related Art

Infusion pumps are medical devices that deliver fluids, including nutrients and medications such as antibiotics, chemotherapy drugs, and pain relievers, into a patient's body in controlled amounts. Many types of pumps, including large volume, patient-controlled analgesia (PCA), elastomeric, syringe, enteral, and insulin pumps, are used worldwide in healthcare facilities, such as hospitals, and in the home. Clinicians and patients rely on pumps for safe and accurate administration of fluids and medications.

More than 90 percent of surgical patients and one-third of non-surgical patients receive some form of intravenous therapy while in the hospital. Industry reports indicate an estimated 400,000 drug related injuries occur in hospitals annually generating $3.5 billion in extra medical costs. Safety software, including drug error reduction systems (DERS), has been developed to reduce medication errors, enhance quality care, and improve workflow.

Drug error reduction systems (DERS) typically use a drug library editor (DLE) to develop drug libraries including protocols, rule sets, and/or pump configuration settings, which are then loaded onto an infusion pump. The drug library at the infusion pump provides medication pick lists for the caregiver to select the desired therapy, medication profiles including hard and soft limits, and pump configuration settings including but not limited to distal pressure occlusion limits, air-in-line limits, callback settings, backlight display settings, etc.

Drug library editors are currently one of two types: dedicated DLEs or enterprise DLEs. Dedicated DLEs can only be connected to one infusion pump at a time to download the drug library to the individual infusion pump. Enterprise DLEs are part of an integrated healthcare facility system and can be connected to download a drug library to a number of infusion pumps.

Dedicated DLEs for a single type of infusion pump can implement drug error reduction systems in a simple cost-effective manner, but typically have reduced functionality when compared to enterprise DLEs. Dedicated DLEs generally provide protocol based libraries, in which the point of care caregiver selects a predefined protocol from a list, then accepts or modifies the predefined infusion parameters for the infusion to be administered. Dedicated DLEs work well for home, nursing homes, and other smaller facilities in which a limited number of medications are used.

Enterprise DLEs for multiple infusion pumps can implement drug error reduction systems as part of more complex and expensive systems having large drug libraries, rich functionality, and sophisticated reporting tools. Enterprise DLEs can be used to provide drug profile-based libraries, with the point of care caregiver selecting a medication from a medication list, then programming the infusion to be administered under limits assigned to the medication. Enterprise DLEs work well for hospitals, treatment centers, surgery centers, and other large facilities.

Unfortunately, no infusion pump is presently available which is able to obtain drug libraries from different types of drug library editors, e.g., from both dedicated DLEs and enterprise DLEs. Although in the case of enterprise DLEs, one DLE may be used with different types of infusion pumps, no infusion pump can receive drug libraries from more than one DLE even though one infusion pump type can be used in different settings, such as the home or hospital. In present practice, one infusion pump can receive a drug library from one specified type of drug library editor, but no other. For example, one infusion pump can receive a drug library from an enterprise drug library editor, but not a dedicated drug library editor. Similarly, a different kind of infusion pump can receive a drug library from a dedicated drug library editor, but not an enterprise drug library editor. Thus, the manufacturer must produce and the users must select different infusion pumps and associated DLEs for different applications, increasing cost and complexity. Different programming is required for dedicated DLEs and enterprise DLEs, increasing the confusion and effort required for programmers of different DLEs.

Healthcare systems which cover multiple levels of care from home care to hospital care must maintain different DLEs for different levels, increasing costs to the healthcare system and to the consumers.

It would be desirable to have infusion pump systems and methods with multiple drug library editor source capability that would overcome the above disadvantages.

SUMMARY OF THE INVENTION

One aspect of the present invention provides an infusion pump system including a first drug library editor operable to generate a first drug library; a second drug library editor operable to generate a second drug library; and an infusion pump operable to connect to either one of the first drug library editor and the second drug library editor, the infusion pump having an operational drug library being one of the first drug library received from the first drug library editor and the second drug library received from the second drug library editor. The first drug library editor is one of a dedicated drug library editor and an enterprise drug library editor, and the second drug library editor is the other of the one of the dedicated drug library editor and the enterprise drug library editor.

Another aspect of the present invention provides a method of configuring one or more infusion pumps including providing an infusion pump having an operational drug library; preparing a first drug library on a first drug library editor; loading the first drug library into the infusion pump from the first drug library editor as the operational drug library; delivering an infusion from the infusion pump in accordance with the first drug library; preparing a second drug library on a second drug library editor; loading the second drug library into the infusion pump from the second drug library editor as the operational drug library; and delivering an infusion from the infusion pump in accordance with the second drug library. The first drug library editor is one of a dedicated drug library editor and an enterprise drug library editor, and the second drug library editor is the other of the one of the dedicated drug library editor and the enterprise drug library editor.

Another aspect of the present invention provides a method of configuring one or more infusion pumps including providing an infusion pump adapted to receive a drug library from one of multiple drug library editors and having an operational drug library; preparing one of a first drug library on a first drug library editor or a second drug library on a second drug library editor.

selecting one of the first drug library editor and the second drug library editor as a source for a received drug library; loading the received drug library into the infusion pump as the operational drug library; and delivering an infusion from the infusion pump in accordance with the operational drug library, wherein the first drug library editor is one of a dedicated drug library editor and an enterprise drug library editor, and the second drug library editor is the other of the one of the dedicated drug library editor and the enterprise drug library editor.

Yet another aspect of the present invention provides an infusion pump for selectable use with either one of a first drug library editor operable to generate a first drug library and a second drug library editor operable to generate a second drug library, the first drug library editor being one of a dedicated drug library editor and an enterprise drug library editor, and the second drug library editor being the other of the one of the dedicated drug library editor and the enterprise drug library editor. The infusion pump includes a memory operable to store an operational drug library; a flow controller operably connected to the memory; and a fluid driver operably connected to the flow controller. The memory is operable to receive a selection of one of the first drug library from the first drug library editor and the second drug library from the second drug library editor as the operational drug library, and the flow controller is operable to control the fluid driver in accordance with the received operational drug library.

The foregoing and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

Like elements share like reference numbers throughout the various figures.

DETAILED DESCRIPTION OF THE
PREFERRED EMBODIMENT

An infusion pump system with multiple drug library editor source capability is described herein. The infusion pump can receive an operational drug library from either one of a dedicated drug library editor or an enterprise drug library editor. Thus, the infusion pump can be used with a medication management system such as used in a large enterprise medical care facility like a hospital or in a small dedicated care facility such as a nursing home or the home of a patient.

Figure 1:
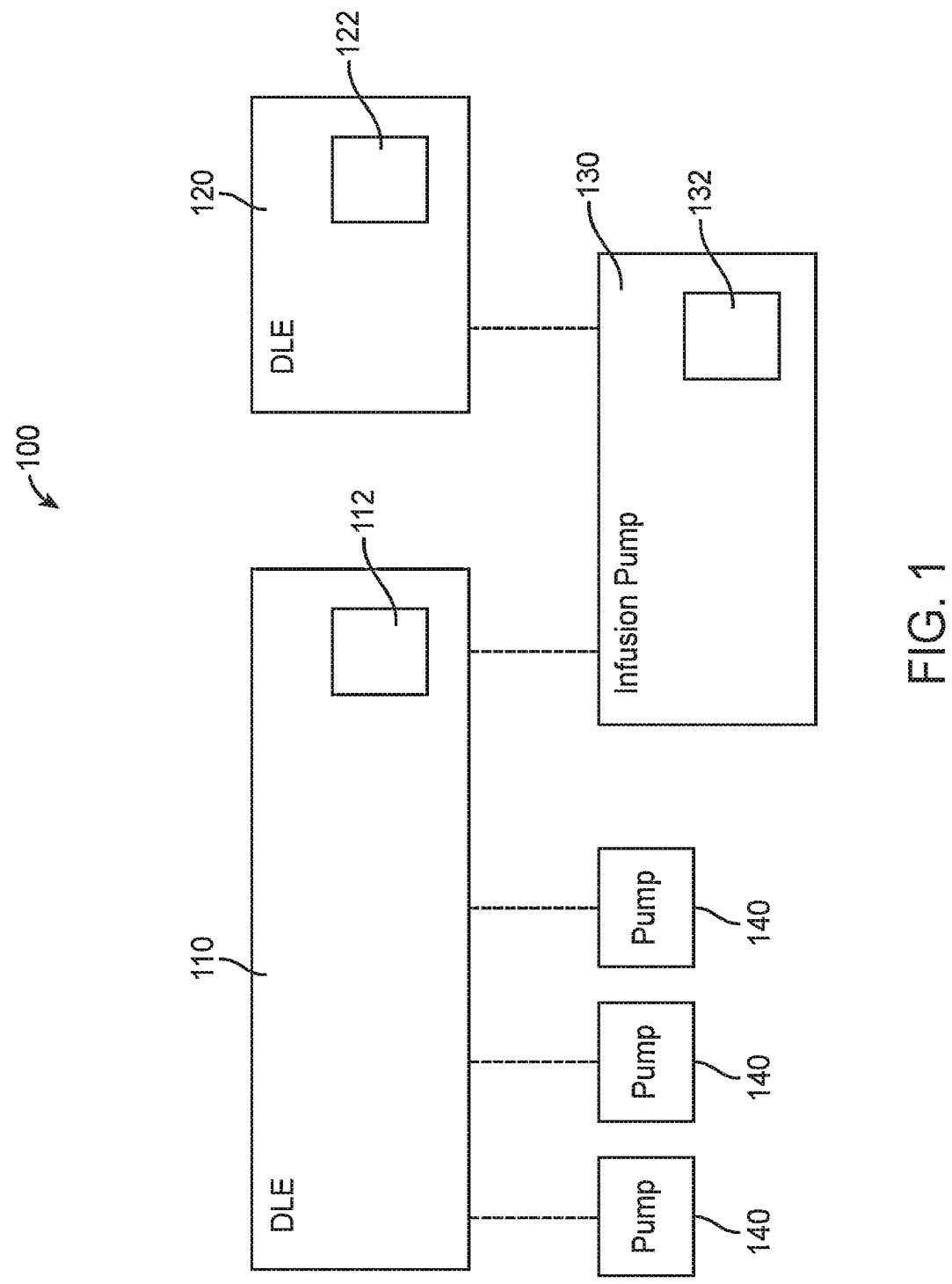
FIG. 1 is a block diagram of an infusion pump system with multiple drug library editor source capability in accordance with the present invention.

FIG. 1 is a block diagram of an infusion pump system with multiple drug library editor source capability in accordance with the present invention. In this example, the infusion pump system includes a dedicated drug library editor and an enterprise drug library editor. The infusion pump provides a therapeutic fluid from a fluid reservoir to a patient in accordance with operating parameters and/or limits established in an operational drug library.

An infusion pump system 100 includes a first drug library editor (DLE) 110, a second drug library editor (DLE) 120, and an infusion pump 130. The first drug library editor 110 is operable to generate a first drug library 112 and the second drug library editor 120 is operable to generate a second drug library 122. The infusion pump 130 is operable to connect to either one of the first drug library editor 120 or the second drug library editor 130 as desired for a particular application. The infusion pump 130 has an operational drug library 132, which is one of the first drug library 112 received from the first drug library editor 110 or the second drug library 122 received from the second drug library editor 120. The first drug library editor 110 is one of a dedicated drug library editor and an enterprise drug library editor, and the second drug library editor 120 is the other of the one of the dedicated drug library editor and the enterprise drug library editor. Thus, one drug library editor is of one type and the other drug library editor is of a different type.

Figure 2:
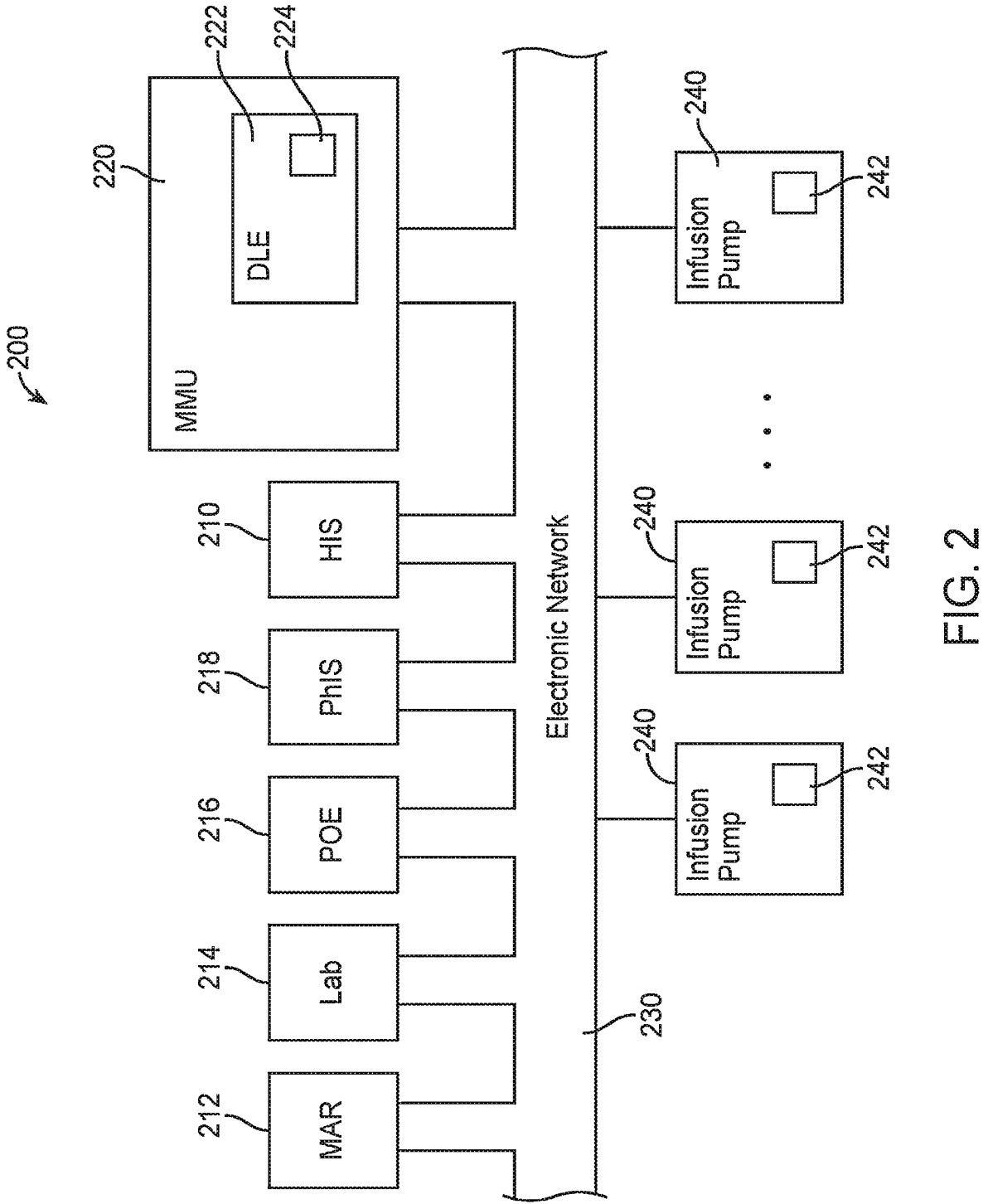
FIG. 2 is a block diagram of a medication management system with an enterprise drug library editor for an infusion pump system with multiple drug library editor source capability in accordance with the present invention.

In this example, the first drug library editor 110 is the enterprise drug library editor and the second drug library editor 120 is the dedicated drug library editor. The first drug library editor 110 can provide operational drug libraries to a number of infusion pumps 140 in addition to the infusion pump 130. The enterprise drug library editor 110 is part of a medication management unit 220 that is in electronic communication or networked with other electronic information systems within a healthcare system, which facilitates or provides bi-directional communication between the pumps and the other electronic information systems, as best seen in FIG. 2. The second drug library editor 120 only provides drug libraries to one infusion pump at a time, in this case infusion pump 130. The dedicated drug library editor 120 as defined herein is a standalone drug library editor that is not networked to other information systems within a healthcare system. The dedicated drug library editor is operably connectable to and provides a drug library for a single type of infusion pump, typically a limited set of local infusion pumps such as one to fifteen infusion pumps in a single geographic location. The dedicated drug library editor is also limited in the functions it performs and typically only handles the creation, editing and downloading of a drug library to the pump. The enterprise drug library editor as defined herein is a drug library editor operably connectable to and providing drug libraries for a number of different types of infusion pumps, for example a multitude (more than fifteen) geographically dispersed pumps of various types (PCA, syringe, large volume parenteral, etc.). The enterprise drug library editor is typically a part of a larger suite of software applications run on or connected through a client computer to a server that has more functions such as bi-directional communications between the pump and server, as well as sophisticated logging and reporting on pump programming, user input, and operation (including but not limited to alarms, alerts, messages, overrides, program modifications, etc.). The application of the dedicated drug library editor and the enterprise drug library editor are described below in association with FIGS. 2 & 3, respectively.

Referring to FIG. 1, the first drug library editor 110 and second drug library editor 120 are operably connectable to the infusion pump 130 as indicated by the dashed lines between the drug library editors 110, 120 and the infusion pump 130. The connections between the drug library editors 110, 120 and the infusion pump 130 can be wired, wireless, or a combination of wired and wireless. For the enterprise drug library editor, the connections between the drug library editors 110, 120 and the infusion pump 130 can include intermediate components as desired for a particular application. One of the drug library editors 110, 120 can be connected to the infusion pump 130 to transfer the drug library 112, 122, respectively, to the infusion pump 130 as the operational drug library 132, and then the connection between the drug library editor and the infusion pump can be disconnected.

The first drug library editor 110 and second drug library editors 120 are used to create and/or modify the first drug library 112 and the second drug library 122, respectively. The drug library editor operates on the drug library within the drug library editor to support, maintain, edit, and/or export the operational drug library received by the infusion pump. A programmer (not shown), such as a licensed pharmacist, doctor, biomedical engineer, or the like, working with the drug library editor on a user interface can create and/or modify the drug libraries as desired for a particular application. The drug library editor can be deployed in a medication management system on one or more computers and enables the programmer to import, export, and edit whole drug libraries and individual drug library values to control and customize a drug library according to hospital preferences. In one example, drug libraries in the drug library editor can be formulated and edited using a conventional database management software platform, such as SQL Server or SQL Desktop Engine by Microsoft of Redmond, Washington.

The first drug library 112 and the second drug library 122 can each be part of a customizable drug library database available to the first drug library editor 110 and second drug library editors 120, respectively. The drug library includes drug and infusion pump related information, which may include but is not limited to drug name, drug class, drug concentration, drug amount, drug units, diluent amount, diluent units, dosing units, delivery dose or rate, medication parameters or limits (hard or soft), device/infuser settings and/or modes, clinical care area (CCA) designations and constraints, library version, and the like. The drug library can also include operating parameters for reporting from each of the infusion pumps back to the medication management system.

FIG. 2 is a block diagram of a medication management system 200 with an enterprise drug library editor for an infusion pump system with multiple drug library editor source capability in accordance with the present invention. The enterprise drug library editor is a drug library editor operably connectable to and providing drug libraries for a multitude of infusion pumps, for example more than fifteen pumps. One example of an enterprise drug library editor 222 is the Hospira MedNet™ Meds™ drug library editor from Hospira, Inc. of Lake Forest, Ill., U.S.A. The infusion pumps served by the enterprise drug library editor are typically of various different types. Types in this context can mean different operating mechanisms, manufacturers, models, or software or hardware versions, by way of example and not limitation.

The medication management system 200 provides an integrated enterprise-wide medication management system that reduces the risks of medication error and improves patient safety. The medication management system (MMS) 200 includes a hospital information system (HIS) 210, a medication management unit (MMU) 220, an electronic network 230, and infusion pumps 240. In one embodiment, the medication management system (MMS) 200 operates in a hospital environment which can be construed broadly as used herein to mean any medical care facility, including but not limited to a hospital, treatment center, clinic, doctor's office, day surgery center, hospice, nursing home, and any of the above associated with a home care environment. In one embodiment, the medication management system 200 operates in a large medical care facility, such as a hospital or treatment center. The medication management unit 220 deployed on one or more enterprise servers includes a drug library editor 222 with a drug library 224. Each of the infusion pumps 240 includes an operational drug library 242, with each of the operational drug libraries 242 for each individual infusion pump 240 being tailored for the patient using each individual infusion pump 240, i.e., the operational drug libraries 242 can be different from each other as required to meet the therapy needs of a particular patient, the intended use of the infusion pump, or the location of the pump or patient. The medication management system 200 can include one or more computers/servers with associated software as required for a particular application.

The medication management system (MMS) 200 can optionally include additional information systems in communication with the medication management unit (MMU) 220 and infusion pumps 240 across the electronic network 230. In various embodiments, the medication management system (MMS) 200 can optionally include a pharmacy information system (PhIS) 218 for delivering drug orders to a hospital information system (HIS) 210, a physician/provider order entry (POE) 216 permitting a healthcare provider to deliver a medication order prescribed for a patient to the hospital information system, a lab system 214 to monitor patient data and to deliver updated patient-specific information such as lab tests, measurements or the like to the MMU 220, and/or a medication administration record system (MAR) 212 for maintaining medication records. The medication management system (MMS) 200 can also include monitoring devices (not shown) in communication with the MMU 220 and/or lab system 214, for monitoring condition of the patient using each of the infusion pumps 240.

The hospital information system (HIS) 210 can be any information system operable to communicate across the hospital environment. The hospital information system 210 can include and/or communicate with the medication administration record system (MAR) 212 to maintain medication records and the pharmacy information system (PhIS) 218 to deliver drug orders to the hospital information system 210. The physician/provider order entry (POE) device 216 can permit a healthcare provider to deliver a medication order prescribed for a patient to the hospital information system 210 directly or indirectly via the PhIS 218. One skilled in the art will also appreciate that a medication order can be sent to the MMU 220 directly from the PhIS 218 or POE device 216. As used herein the term medication order is defined as an order or "prescription" to administer something that has a physiological impact on a person or animal, including but not limited to liquid or gaseous fluids, drugs or medicines, liquid nutritional products and combinations thereof.

The medication management unit 220 includes the drug library editor 222 with a drug library 224. The drug library editor 222 operates on the drug library 224 within the drug library editor 222 to support, maintain, edit, import and/or export the operational drug library received by the infusion pumps 240. A programmer (not shown), such as a licensed pharmacist, doctor, or the like, can work with the drug library editor on a user interface to create and/or modify the drug library 224 as desired for a particular application. The drug library editor 222 can be deployed in the medication management unit 220 on one or more computers and enables the programmer to import, export, and edit whole drug libraries and individual drug library values to control and customize a drug library according to hospital preferences.

The medication management unit 220 can perform other functions in addition to being the drug library editor. In one embodiment, the medication management unit 220 can further maintain patient safety by reviewing medication orders, drug-drug compatibility, and medication delivery time sequences. In another embodiment, the medication management unit 220 can modulate performance of a medication order based on laboratory data or other newly received patient information. In another embodiment, the medication management unit 220 can monitor the status of the infusion pumps and infusion status progress (including alarms, event logs, and pump user interface inputs), generate reports, and control software or operating code updates to the infusion pumps.

The electronic network 230 can be any information network operable to connect the hospital information system (HIS) 210, medication management unit (MMU) 220, and infusion pumps 240. The electronic network 230 can be any combination of wired and/or wireless networks as desired for a particular application. The electronic network 230 can provide communication within a single location, such as a single hospital, or can provide communication over various geographic locations, such as a healthcare network.

The infusion pumps 240 include one or more infusion pumps with multiple drug library editor source capability. The infusion pumps 240 can be any type of pump, including but not limited to a pump having a pumping mechanism or fluid driver, which acts upon a cassette, reservoir, vial, syringe, or tubing to convey medication or fluid to or from a patient. Exemplary pumps include but are not limited to enteral pumps, infusion pumps, patient controlled analgesia (PCA) or pain management medication pumps, syringe pumps, peristaltic pumps and the like. The pumps could be stationary (pole or bedside mounted and plugged into an AC outlet) or ambulatory (worn or carried by the patient and power by one or more batteries) or some combination of these types or individual features. In one embodiment, the infusion pump with multiple drug library editor source capability can be an infusion pump as described below in association with FIG. 4.

The Hospira MedNet™ safety software available from Hospira, Inc., of Lake Forest, Ill., U.S.A. is one example of software that resides in the medication management unit or MMU 220 of a medication management system 200. The Hospira MedNet™ safety software is described in U.S. patent application Ser. No. 10/930,358 filed Aug. 31, 2004, entitled Medication Management System (now U.S. Pat. No. 7,895,053, issued Feb. 22, 2011), incorporated herein in its entirety by reference. The Hospira MedNet™ safety software links infusion devices with the hospital pharmacy and hospital information systems, enabling clinicians to better bi-directionally communicate, understand and manage IV infusion information with respect to infusion pumps at the point of care. As stated above, one example of an enterprise drug library editor is Hospira MedNet™ Meds™ software. An early version of such software is described in U.S. Pat. No. 8,065,161 to Howard et al., entitled System for Maintaining Drug Information and Communicating with Medication Delivery Devices, which is incorporated herein in its entirety by reference. Using such a drug library editor, hospital pharmacists work in collaboration with a cross-functional medical team to develop customized drug libraries and dose recommendations, which are then programmed into a database and transferred to the infusion pump. The drug libraries can incorporate both hard and soft dose limits, and can customize clinical decision rules for multiple clinical care areas (CCAs). In various applications, the Hospira MedNet™ safety software and Hospira MedNet™ Meds™ drug library editor software can be used with the Hospira Plum A+™ general infusion system, the Hospira Plum A+™ 3 triple-channel device, the Hospira LifeCare PCA™ patient-controlled analgesia system, or the Hospira Symbig™ infusion pump.

Figure 3:
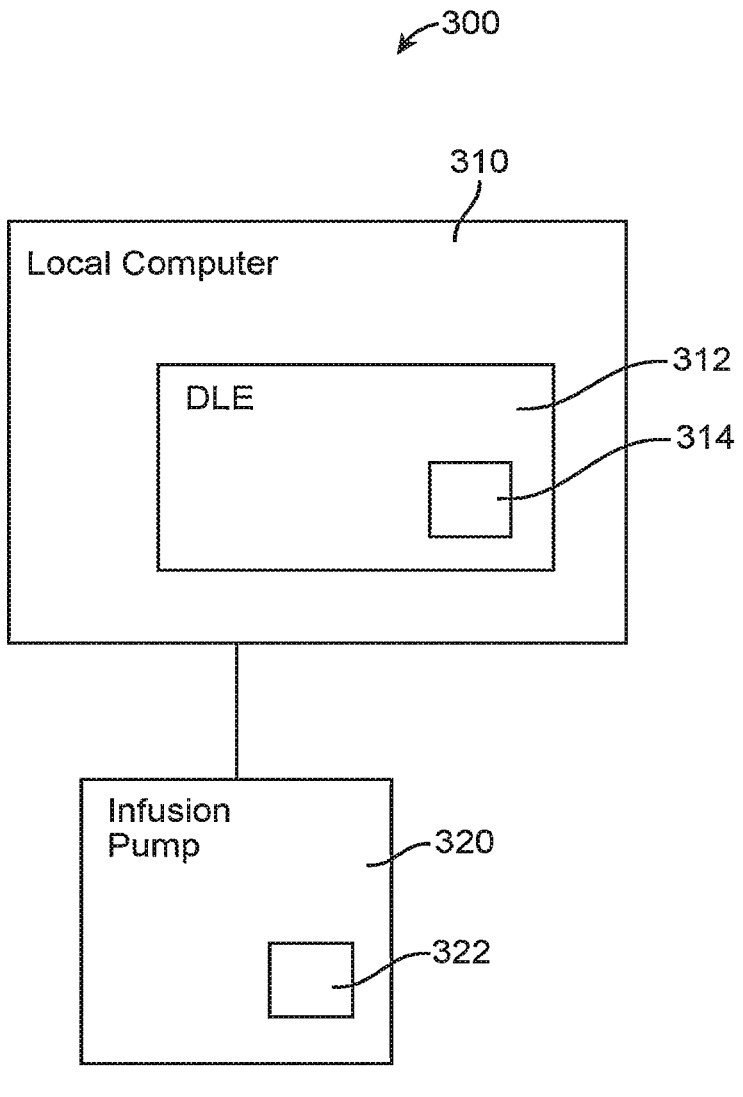
FIG. 3 is a block diagram of a dedicated infusion pump system with a dedicated drug library editor for an infusion pump system with multiple drug library editor source capability in accordance with the present invention.

FIG. 3 is a block diagram of an infusion pump system with a standalone, dedicated drug library editor for an infusion pump system with multiple drug library editor source capability in accordance with the present invention. The dedicated drug library editor is a drug library editor operably connectable to and providing a drug library for a single type of infusion pump or a limited set of from one to fifteen infusion pumps of the same type.

The infusion pump system 300 includes a local computer 310 and an infusion pump 320. A dedicated drug library editor 312 having a drug library 314 is deployed on the local computer 310. The infusion pump 320 includes an operational drug library 322. In one embodiment, both the local computer 310 and infusion pump 320 are located at the point of care (POC) of the patient, such as a hospice, nursing home, home care environment, or the like. In another embodiment, the local computer 310 is located in a non-patient care area such as a biomedical engineering area and is used to setup or configure infusion pumps for distribution and use in other locations. In one embodiment, the infusion pump system 300 can provide various exemplary therapies, such as continuous therapy, multistep therapy, intermittent therapy, total parenteral nutrition (TPN), Patient Controlled Analgesia (PCA) therapy, epidural therapy, or the like.

The local computer 310 can be any computing device capable of deploying the dedicated drug library editor 312 as desired for a particular application. Exemplary computing devices include personal computers, tablet computers, personal digital assistants, handheld computers, and the like. The local computer 310 can communicate with the infusion pump 320 when connected to the infusion pump 320 over wired or wireless connections.

The infusion pump 320 is an infusion pump with multiple drug library editor source capability. The infusion pumps 320 can be any type of pump, including but not limited to a pump having a pumping mechanism or fluid driver, which acts upon a cassette, reservoir, vial, syringe, or tubing to convey medication or fluid to or from a patient. Exemplary pumps include but are not limited to enteral pumps, infusion pumps, patient controlled analgesia (PCA) or pain management medication pumps, syringe pumps, peristaltic pumps and the like. In one embodiment, the infusion pump with multiple drug library editor source capability can be an infusion pump as described below in association with FIG. 4.

Exemplary medication management systems with stand-alone, dedicated drug library editors deployed on or used on a standalone local computer include the GemStar™ SP Infusion System from Hospira, Inc., of Lake Forest, Ill.

Figure 4:
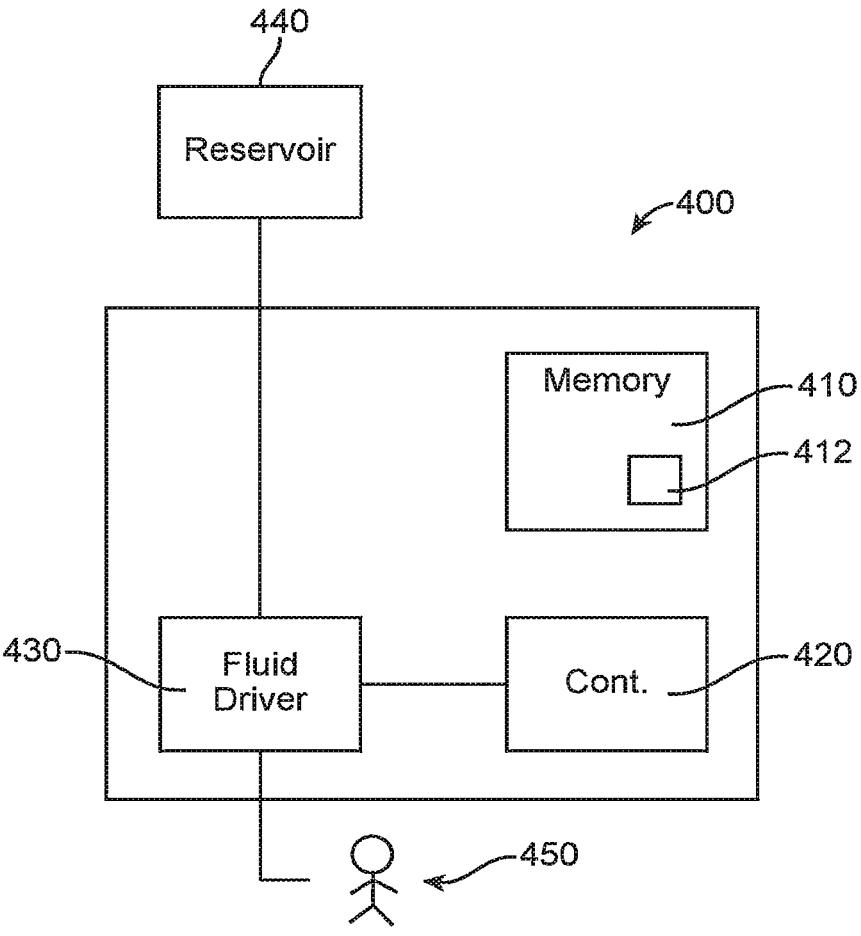
FIG. 4 is a block diagram of an infusion pump with multiple drug library editor source capability in accordance with the present invention.

FIG. 4 is a block diagram of an infusion pump with multiple drug library editor source capability in accordance with the present invention. The infusion pump can receive an operational drug library from either one of a dedicated drug library editor or an enterprise drug library editor.

The infusion pump 400 is for selective use with either one of a first drug library editor or a second drug library editor as described above. The first drug library editor is operable to generate a first drug library and the second drug library editor is operable to generate a second drug library. One of the first drug library editor and the second drug library editor is a dedicated drug library editor operably connectable to and providing a drug library for a single infusion pump or a single type of infusion pump. The other of the first drug library editor and the second drug library editor is an enterprise drug library editor operably connectable to and providing drug libraries for a large number of infusion pumps or different types of infusion pumps.

The infusion pump 400 includes a memory 410 operable to store an operational drug library 412, a flow controller 420 operably connected to the memory 410, and a fluid driver 430 operably connected to the flow controller 420. The memory 410 is operable to receive one of the first drug library from the first drug library editor and the second drug library from the second drug library editor as the operational drug library 412. The flow controller 420 is operable to control the fluid driver 430 in accordance with the received operational drug library 412 and delivering the infusion to the patient 450. In one embodiment, the infusion pump 400 delivers the infusion from a fluid reservoir 440 to the patient 450. In one embodiment, the fluid driver 430 acts upon a fluid containing device, such as a cassette, reservoir, vial, syringe, tubing, or the like, to convey medication or fluid to or from a patient.

Figure 5:
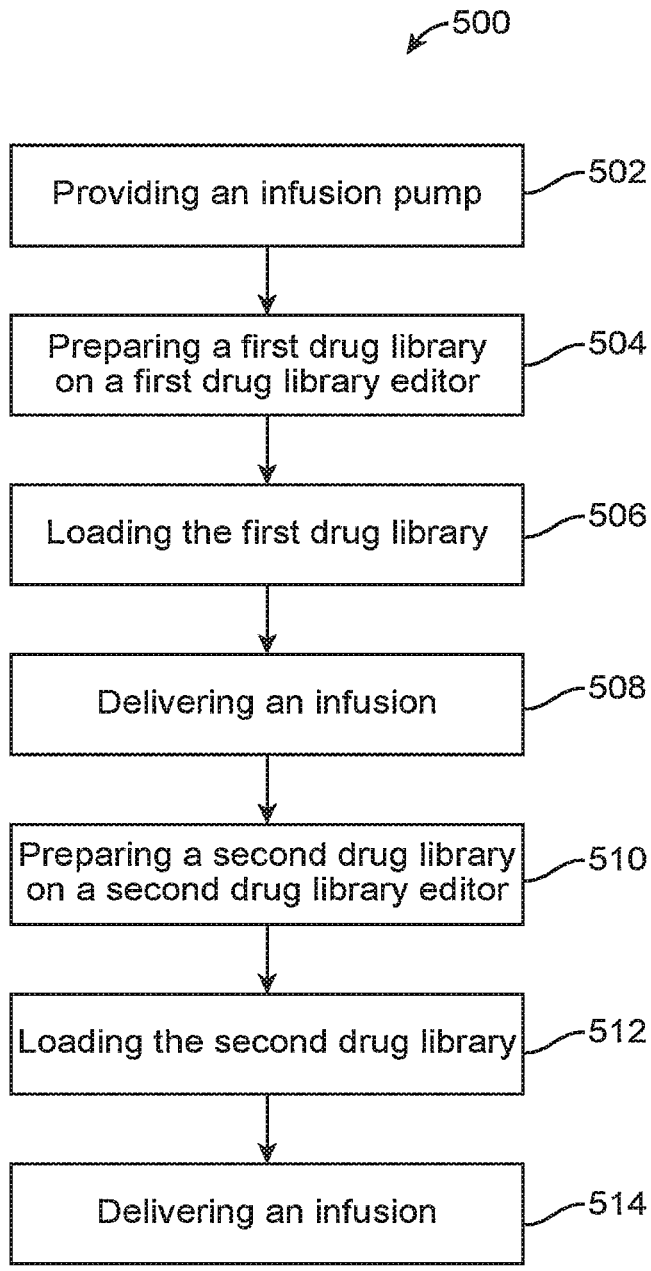
FIG. 5 is a flowchart of a method of use for an infusion pump system with multiple drug library editor source capability in accordance with the present invention.

FIG. 5 is a flowchart of a method of use for an infusion pump system with multiple drug library editor source capability in accordance with one embodiment of the present invention. The method can be used with the infusion pump system and infusion pump described above in conjunction with FIGS. 1-4.

Referring to FIG. 5, the method 500 includes providing an infusion pump 502 having an operational drug library; preparing a first drug library on a first drug library editor 504; loading the first drug library 506 into the infusion pump from the first drug library editor as the operational drug library; delivering an infusion 508 from the infusion pump in accordance with the first drug library; preparing a second drug library on a second drug library editor 510; loading the second drug library 512 into the infusion pump from the second drug library editor as the operational drug library; and delivering an infusion 514 from the infusion pump in accordance with the second drug library. The first drug library editor is one of a dedicated drug library editor and an enterprise drug library editor, and the second drug library editor is the other of the one of the dedicated drug library editor and the enterprise drug library editor.

In one embodiment, the first drug library editor is the dedicated drug library editor deployed on a local computer operably connectable to and local to the infusion pump. The local computer can be a personal computer, tablet computer, personal digital assistant, handheld computer, or the like. In one embodiment, the delivering an infusion 508 from the infusion pump in accordance with the first drug library further includes delivering the infusion from the infusion pump at a location such as a hospice, a nursing home, a home care environment, or other small treatment location.

In one embodiment, the infusion pump is one of a large number or multitude of infusion pumps or plurality of types of infusion pumps and the first drug library editor is the enterprise drug library editor deployed on a medication management unit operably connectable to and remote from the multitude of infusion pumps or plurality of types of infusion pumps. In one embodiment, the first drug library editor is the enterprise drug library editor deployed on a medication management unit operably connectable to and remote from the infusion pump, and the delivering an infusion 508 from the infusion pump in accordance with the first drug library further includes delivering the infusion from the infusion pump at a location such as a hospital, a treatment center, or other large treatment location.

Figure 6:
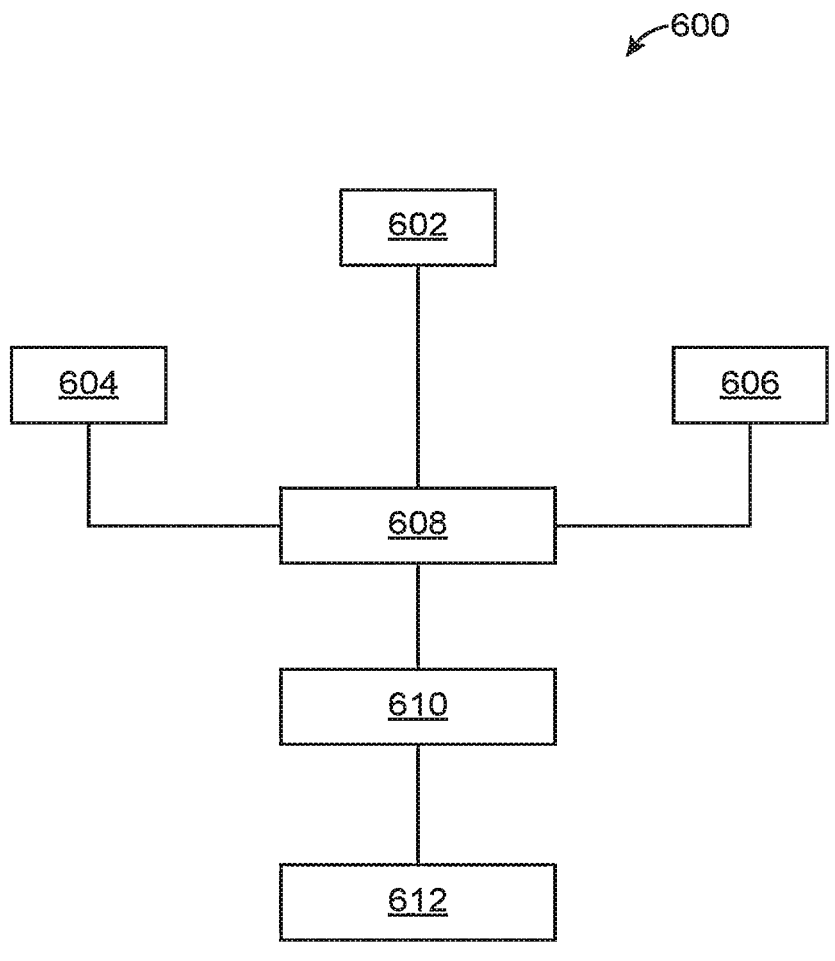
FIG. 6 is a flowchart of another method of use for an infusion pump system with multiple drug library editor source capability in accordance with the present invention.

FIG. 6 is a flowchart of another embodiment of a method of use for an infusion pump system with multiple drug library editor source capability in accordance with the present invention. The method can be used with the infusion pump system and infusion pump described above in conjunction with FIGS. 1-4.

Referring to FIG. 6, the method 600 includes the step 602 of providing an infusion pump with multiple drug library editor source capability; preparing in step 604 a first drug library using a first drug library editor and/or preparing in step 606 a second drug library using a second drug library editor; selecting in step 608 a source drug library editor from one of the first drug library editor and the second drug library editor; loading in step 610 one of the first drug library and the second drug library into the infusion pump from the selected source drug library editor as an operational drug library; and in step 612 operating the infusion pump in accordance with the loaded operational drug library, in other words using the configuration and operational parameters defined in the operational drug library.

In one embodiment of the method 600 the step 608 of selecting a source drug library editor is performed at the infusion pump by a user making a selection from a plurality of possible selections on a user interface of the pump. In one embodiment, a download drug library function could be facilitated by a pump user interface display screen with a drop-down menu of drug library editor sources. The operational drug library is requested by the infusion pump to be downloaded from the selected source drug library editor. In another embodiment, the selecting of the source drug library editor is performed at one of the first and second drug library editors by a user of the drug library editors. A drug library editor user interface display screen can provide a drop-down menu or other means of selection for the drug library editor source. Then the selected drug library editor source can download the respective drug library to the target pump or pumps. In another embodiment, a special handshake between the drug library editor and the pump could identify the drug library editor source selected at the drug library editor. The download message or drug library itself could contain a code, configuration setting or direction as to where to accept the next drug library from. In yet another embodiment, the selection of the source drug library editor is performed at the medication management unit (MMU) depending on healthcare facility preferences and practices for a given infusion pump or set of infusion pumps.

One advantage of the present invention is that it provides a way to migrate one or more pumps from a dedicated drug library editor system to an enterprise drug library editor system without having to change out the pumps. It is also possible to remove pumps from an enterprise drug library editor environment and place them in a dedicated drug library environment like an alternative care site, nursing home, or patient's home without changing the pump. This seamless repurposing of pumps makes their inventory and associated capital costs easier to manage. Finally, the present invention allows the dedicated drug library editor to be more focused and therefore optimized in its limited functions for the type of pump it serves. The less complex dedicated drug library editor would be less costly to produce (and purchase), easier to setup, understand and run. Conversely, an enterprise drug library editor can be more easily life cycle managed, such as upgraded with bug fixes, new components or additional functionality, pump types, etc. The present invention allows for the leveraging of the advantages of both types of drug library editors in a single pump with multiple drug library editor capability.

While the embodiments of the invention disclosed herein are presently considered to be preferred, various changes, rearrangement of steps, and modifications can be made without departing from the scope of the invention. The scope of the invention is indicated in the appended claims, and all changes that come within the meaning and range of equivalents are intended to be embraced therein.

What is claimed is:

1. An infusion pump for selectable use with either one of a first drug library editor operable to generate a first drug library and a second drug library editor operable to generate a second drug library, the first drug library editor being one of a dedicated drug library editor and an enterprise drug library editor, and the second drug library editor being the other of the one of the dedicated drug library editor and the enterprise drug library editor, the infusion pump comprising:

a memory operable to store an operational drug library;

a flow controller operably connected to the memory; and a fluid driver operably connected to the flow controller;

wherein the memory is operable to receive a selection of one of the first drug library from the first drug library editor and the second drug library from the second drug library editor as the operational drug library; and the flow controller is operable to control the fluid driver in accordance with the received operational drug library, wherein the operational drug library further comprises a configuration setting that indicates where to accept a next drug library corresponding to one of the first and second drug library editors.

2. The infusion pump of claim 1 wherein the first drug library editor is the dedicated drug library editor deployed on a local computer operably connectable to and local to the infusion pump.

3. The infusion pump of claim 1 wherein the infusion pump is one type of a plurality of different types of infusion pumps and wherein the first drug library editor is the enterprise drug library editor deployed on a medication management unit operably connectable to and remote from the plurality of different types of infusion pumps.

4. The infusion pump of claim 1 wherein the fluid driver is operable to act on a fluid containing device selected from the group consisting of a cassette, reservoir, vial, syringe, and tubing.

5. The infusion pump of claim 1 wherein a signal regarding the selection of one of the first drug library from the first drug library editor and the second drug library from the second drug library editor is generated at the infusion pump through user selection on a user interface of the infusion pump.

* * * * *